United States Patent
Pulkkinen et al.

(10) Patent No.: US 9,278,942 B2
(45) Date of Patent: Mar. 8, 2016

(54) NON-STEROIDAL COMPOUNDS AS ANDROGEN RECEPTOR MODULATORS

(71) Applicant: FLX Discoveries Oy, Kuopio (FI)

(72) Inventors: Juha Pulkkinen, Kuopio (FI); Pekka Poutiainen, Kuopio (FI); Tuomas Oravilahti, Kuopio (FI); Jorma Palvimo, Kuopio (FI); Mikael Perakyla, Kuopio (FI); Reino Laatikainen, Kuopio (FI); Tarja Ihalainen, Kuopio (FI)

(73) Assignee: FLX Discoveries Oy, Kuopio (FI)

( * ) Notice: Subject to any disclaimer, the term of this patent is extended or adjusted under 35 U.S.C. 154(b) by 0 days.

(21) Appl. No.: 14/352,052

(22) PCT Filed: Oct. 17, 2012

(86) PCT No.: PCT/FI2012/050995
§ 371 (c)(1),
(2) Date: Apr. 15, 2014

(87) PCT Pub. No.: WO2013/057372
PCT Pub. Date: Apr. 25, 2013

(65) Prior Publication Data
US 2014/0275186 A1    Sep. 18, 2014

(30) Foreign Application Priority Data
Oct. 18, 2011    (FI) ...................................... 20116033

(51) Int. Cl.
*C07D 261/04*    (2006.01)
*C07D 261/20*    (2006.01)
*C07D 271/06*    (2006.01)

(52) U.S. Cl.
CPC ............ *C07D 261/04* (2013.01); *C07D 261/20* (2013.01); *C07D 271/06* (2013.01)

(58) Field of Classification Search
CPC ........................... C07D 261/04; C07D 261/20
See application file for complete search history.

(56) References Cited

FOREIGN PATENT DOCUMENTS

| | | | |
|---|---|---|---|
| EP | 409273 | A | 1/1991 |
| EP | 409273 | A2 * | 1/1991 |
| EP | 1553074 | A | 7/2005 |
| WO | 2006085212 | A1 | 8/2006 |
| WO | 2008033513 | A1 | 3/2008 |
| WO | 2009066009 | A1 | 5/2009 |

OTHER PUBLICATIONS

CAPLUS entry for Lakhvich et al. Khimiya Geterotsiklicheskikh Soedinenii (1988), (7), 972-976.*
Baird et al. Tetrahedron 2001, 57, 9849-9858.*
CAPLUS entry for Bianchi et al. Tetrahedron 1970, 26, 5113-5122.*
Kim et al. Bull. Korean Chem. Soc. 1999, 20, 122-124.*
Cancer Research; LNCaP Model of Human Prostatic Carcinoma, Julius S. Horoszewicz, Susan S. Leong, Elzbieta Kawinski, et al., Cancer Res 1983;43:1809-1818; Apr. 1983.
Kim, H.R., et al., Diastereoselective reduction and Grignard reaction of 3-aryltetrahydocyclopenta[d]isoxazol-4-ones. Bull. Korean Chem.Soc., 1999, vol. 20(1), pp. 122-124.
Hershenson, F.M., Reactions of 2,4-dichlorobenzonitrile oxide with enolizable Schiff bases, J. Heterocyclic Chem., 1972, vol. 9(3), pp. 739-740.
Walters, M.J., et al., The preparation of 5-aryl-5-methyl-4,5-dihydroisoxazoles from dithiated C(alpha)O-oximes and select acetyl ketones, Synth.Commun., 2003, vol. 33(23), pp. 4163-4171.
Poutiainen, P.K., et al, Design, Synthesis, and Biological Evaluation of Nonsteroidal Cycloalkane[d]isoxazoleContaining Androgen Receptor Modulators, J.Med.Chem., 2012, vol. 55(14), pp. 6316-6327 (Published Feb. 7, 2012).
Adembri, et al., A.J.Chem.Soc., Perkin Trans. 1 2000, 2649-2656.
Barbulescu, et al., Rom.Rev.Chim. 1971, 22, 133-136.
Becker, K.B., et al., Helv.Chim. Acta 1979, 62, 2025-2036.
Curran, D.P., et al., Am.Chem.Soc. 1987, 109, 3036-3040.
Dannhardt, G., et al., I.Sci.Pharm. 1984, 52, 280-290.
Gao, W., et al., Pharmaceut. Res. 2006, 23, 1641-1658.
Gao, W. et al., Chem.Rev. 2005, 105, 3352-3370.
Gao, W. et al., Endocrinology 2005, 146, 4887-4897.
Giurg, M. et al., Polish J. Chem. 1997, 71, 1093-1101.
Hara, T. et al., Cancer Res. 2003, 63, 149-153.
Hatahway, B.A. et al., Molecules 1999, 4, M122-M123.
Horoszewicz, J.S. et al., Cancer Res., 1983, 43, 1809-1818.
Lakhvich, F.A. et al., Khim. Geterotsikl. Soed. 1988, 972-976.
Lauria, F. et al., Gazz. Chim. It. 1964, 94, 478-484.
Martin, S.F. et al., Tetrahedron Lett. 1983, 24, 1337-1340.
Nagarajan, A. et al., Indian J. Chem., Sect. B. 1993, 32, 471-474.
Shankar, B.B. et al., Tetrahedron Lett. 1998, 39, 2447-2448.
Shvekhgheimer, G.A. et al., Tez. Vses. Soveshch. Nitros. 1974, 5, 64-65.
Singh, S.M. et al, Curr. Med. Chem. 2000, 7211-7247.
Srivastava, R.M., et al., Heterocycles 2000, 53, 191-195.
Sun, R. et al., J. Agric. Food Chem. 2011, 59, 4851-4859.
Evelyn C R et al: "Design, Synthesis and prostate cancer cell-based studies of analogs of the Rho/MKL1 transcriptional pathway inhibitor, CCG-1423", Bioorganic & Medicinal Chemistry Letters, Pergamon, Amsterdam, NL, vol. 20, No. 2, Jan. 15, 2010, pp. 665-672, XP026812555, ISSN: 0960-894X, [retrieved on Nov. 18, 2009].
Extended Search Report, European Patent Office, May 27, 2015, Application No. 128416302-1462/2768814 PCT/FI2012050995.

* cited by examiner

*Primary Examiner* — Matthew Coughlin
(74) *Attorney, Agent, or Firm* — Ziegler IP Law Group, LLC

(57) ABSTRACT

This invention relates to novel 4,5-dihydroisoxazoles and 4,5-dihydro[1,2,4]-oxadiazoles of formula (I), to their use as androgenic or antiandrogenic agents or androgen receptor modulators, and to methods of their preparation.

2 Claims, 4 Drawing Sheets

NON-STEROIDAL COMPOUNDS AS ANDROGEN RECEPTOR MODULATORS

FIELD OF THE INVENTION

This invention relates to certain 4,5-dihydroisoxazole and 4,5-dihydro-[1,2,4]oxadiazol derivatives, to their use as androgenic or antiandrogenic agents or androgen receptor modulators, and to methods of their preparation.

BACKGROUND OF THE INVENTION

The nuclear hormone receptor superfamily is a very important target for drug development. Members of this group include androgen, estrogen, progesterone, and glucocorticoid receptors, the activity of which is controlled by ligand binding, as well as constitutive androstane and pregnane X receptors which have an essential role in drug metabolism. Nuclear hormone receptors regulate expression of their target genes, which control the essential metabolic reactions and differentiation processes of cells. Thus, disorders linked to nuclear receptors are of great clinical importance.

Androgens play an essential role in many physiological processes such as controlling the development and maintenance of muscle and skeletal mass as well as fertility in the male [Singh, S. M.; Gauthier, S.; Labrie, F. Curr. Med. Chem. 2000, 7211-7247]. Although non-steroidal AR agonists and antagonists are useful in the treatment of many disorders and diseases, there are no tissue specific selective androgen receptor modulators (SARMs) yet in clinical use. In particular, agonistic SARMs could be employed in the treatment of medical conditions such as hypogonadism caused by the deficiency of androgens and, especially, in the longterm hormone replacement therapy of aging people for the treatment of osteoporosis, loss of muscle mass or muscular power and sexual function disorders of both sexes. On the other hand, antiandrogenic compounds can be utilized against prostate cancer and hyperplasia, acne, cachexia and hirsutism, for example [Gao, W.; Bohl, C. E.; Dalton, J. T. Chem. Rev. 2005, 105, 3352-3370. Gao, W.; Reiser, P. J.; Coss, C. C.; Phelps, M. A.; Kaerbey, J. D.; Miller, D. D.; Dalton, J. T. Endocrinology 2005, 146, 4887-4897. Gao, W.; Kim, J.; Dalton, J. T. Pharmaceut. Res. 2006, 23, 1641-1658].

In conclusion, there is a need for small non-steroidal molecules which can act as agonists or antagonists for nuclear hormone receptors such as AR. We now describe a novel set of compounds which bind to AR, and inhibit its activity as assessed by the function of recombinant AR in reporter gene assays as well as by the analysis of endogenous AR target gene expression in human prostate cancer VCaP and LNCaP cells [Horoszewicz, J. S.; Leong, S. S.; Kawinski, E; Karr, J. P.; Rosenthal, H.; Chu, M.; Mirand, E. A.; Murphy, G. P. Cancer Res., 1983, 43, 1809-1818]. A further group of such compounds is for the first time disclosed to also inhibit the transcriptional activation by W741L-mutated AR in COS1-cells. The W741L mutation has been reported in prostate cancer patients and shown to render clinically most commonly used antiandrogen bicalutamide to an agonist [Hara, T.; Miyazaki, J.; Araki, H.; Yamaoka, M. Kanzaki, N.; Kusaka, M.; Miyamoto, M. Cancer Res. 2003, 63, 149-153].

DESCRIPTION OF THE INVENTION

This invention provides a novel compound of the formula (I)

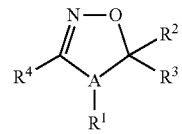

or a stereoisomer, pharmaceutically acceptable salt or a pro-drug form thereof,
wherein
A is carbon or nitrogen;
$R^1$ is hydrogen or alkyl;
$R^2$ is hydrogen, alkyl or phenyl, provided that $R^1$ and $R^2$ cannot simultaneously be hydrogen;
$R^3$ is alkyl or benzyl and may form with $R^1$ a monocyclic aliphatic structure, which may be substituted with a side chain of the formula

wherein n is an integer from 0 to 4, and $R^6$ is hydroxyl, acyloxyl, carboxyl or carboxylate; provided that $R^2$ and $R^3$ cannot simultaneously be alkyl;
$R^4$ is phenyl which is substituted with 1-5 $R^5$, or naphthalen-1-yl, naphthalen-2-yl, benzyl, phenethyl or 3-phenylpropyl which is substituted with 0-5 $R^5$;

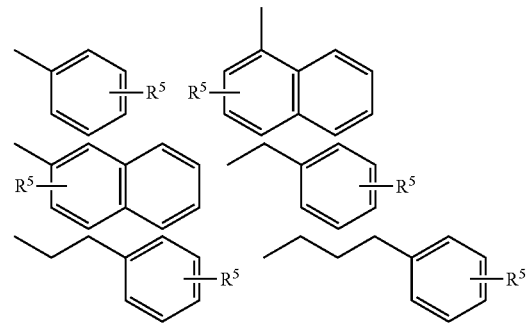

$R^5$ is selected from the group consisting of halogen, nitro, cyano, alkyl, hydroxyl and lower alkoxyl, provided that when $R^4$ is phenyl there can not be more than one hydroxyl or lower alkoxyl simultaneously present as $R^5$ [WO2006085212] and that alkyl or alkoxyl groups may be further substituted by the above mentioned groups; provided that when A is carbon, $R^1$ is hydrogen, $R^2$ is phenyl, and $R^3$ is methyl, then $R^4$ cannot be 3-nitrophenyl or 4-chlorophenyl [Nagarajan, A.; Pillay, M. K. Indian J. Chem., Sect. B. 1993, 32, 471-474.]

when A is carbon, $R^1$ is methyl, $R^2$ is hydrogen, and $R^3$ is methyl, then $R^4$ cannot be 3-nitrophenyl, 4-nitrophenyl or 4-methoxyphenyl [Shvekhgheimer, G. A.; Baranski, A. Tez. Vses. Soveshch. Nitros. 1974, 5, 64-65.]

when A is carbon, $R^1$ is methyl, $R^2$ is hydrogen, and $R^3$ is isopropyl, then $R^4$ cannot be 4-methoxyphenyl or 2,4,6-trimethylphenyl [Martin, S. F.; Dupre, B. Tetrahedron Lett. 1983, 24, 1337-1340.]

when A is carbon, $R^1$ is isopropyl, $R^2$ is hydrogen, and $R^3$ is methyl, then $R^4$ cannot be 4-methoxyphenyl or 2,4,6-trimethylphenyl [Martin, S. F.; Dupre, B. Tetrahedron Lett. 1983, 24, 1337-1340.]

when A is carbon, $R^2$ is hydrogen, and $R^1$ and $R^3$ form together a cyclopentane ring, then $R^4$ cannot be 3-nitrophenyl, 4-nitrophenyl, 4-chlorophenyl, 4-hydroxyphenyl or phenethyl [Nagarajan, A.; Pillay, M. K. *Indian J. Chem., Sect. B.* 1993, 32, 471-474. Barbulescu, N.; Lazar, R. *Rom. Rev. Chim.* 1971, 22, 133-136. Shankar, B. B.; Yang, D. Y.; Girton, S.; Ganguly, A. K. *Tetrahedron Lett.* 1998, 39, 2447-2448. Curran, D. P.; Chao, J.-C. *J. Am. Chem. Soc.* 1987, 109, 3036-3040. Sun, R.; Li, Y.; Xiong, L.; Liu, Y.; Wang, Q. *J. Agric. Food Chem.* 2011, 59, 4851-4859.]

when A is carbon, $R^2$ is hydrogen, and $R^1$ and $R^3$ form together a cyclohexane then $R^4$ cannot be 4-nitrophenyl [Giurg, M.; Mlochowski, J. *Polish J. Chem.* 1997, 71, 1093-1101.]

when A is carbon, $R^2$ is hydrogen, and $R^1$ and $R^3$ form together a cycloheptane or cyclooctane ring then $R^4$ cannot be 4-chlorophenyl [Hathaway, B. A.; Mueller, R. A. *Molecules* 1999, 4, M122-M123.]

when A is carbon, $R^2$ is methyl or phenyl, and $R^1$ and $R^3$ form together a cyclopentane ring, then $R^4$ cannot be 4-nitrophenyl or 4-chlorophenyl [Barbulescu, N.; Lazar, R. *Rom. Rev. Chim.* 1971, 22, 133-136.]

when A is carbon, $R^2$ is methyl, and $R^1$ and $R^3$ form together a cyclopentane or cyclooctane ring then $R^4$ cannot be 2,4,6-trimethylphenyl [Becker, K. B.; Hohermuth, M. K. *Helv. Chim. Acta* 1979, 62, 2025-2036.]

when A is nitrogen, $R^1$ is hydrogen, $R^2$ is phenyl, and $R^3$ is n-butyl, then $R^4$ cannot be 2-chlorophenyl [Srivastava, R. M.; Rosa, M. F.; Eduardo, C.; Carvalho, M.; Portugal, S. da G. M.; Brinn, I. M.; Da Conceicao Pereira, M.; Antunes, O. A. C. *Heterocycles* 2000, 53, 191-195.]

when A is nitrogen, $R^1$ is n-butyl, $R^2$ is hydrogen, and $R^3$ is methyl, then $R^4$ cannot be 4-nitrophenyl or 4-chlorophenyl [Lauria, F.; Vecchietti, V.; Tosolini, G. *Gazz. Chim. It.* 1964, 94, 478-484.]

when A is nitrogen, $R^2$ is phenyl, and $R^1$ and $R^3$ form together a cyclopentane ring, then $R^4$ cannot be 2,4,6-dimethylphenyl or 2,6-dichlorophenyl [Dannhardt, G.; Mayer, K. K.; Sommer, I. *Sci Pharm.* 1984, 52, 280-290.]

when A is carbon, $R^1$ is hydrogen, $R^2$ is methyl and $R^3$ is benzyl, then $R^4$ cannot be 2-, 3- or 4-methoxyphenyl, 2-fluorophenyl, 2-, 3- or 4-chlorophenyl, 4-benzonitrile, or naphthalen-2-yl [WO2009066009]-when A is carbon, $R^1$ is hydrogen, $R^2$ is phenyl and $R^3$ is benzyl, then $R^4$ cannot be 2-, 3- or 4-methoxyphenyl, 2-fluorophenyl, 4-chlorophenyl or 4-nitrophenyl [WO2009066009]

when A is carbon, $R^1$ is hydrogen, $R^2$ is phenyl and $R^3$ is methyl, then $R^4$ cannot be phenethyl, 3-phenyl-propyl, 2-(2-, 3- or 4-hydroxyphenyl)-ethyl or 3-(4-hydroxyphenyl)propyl [WO2009066009].

This invention also provides a novel compound of the formula (II)

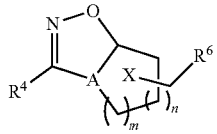

(II)

or a stereoisomer, pharmaceutically acceptable salt or a prodrug form thereof,
wherein
m is an integer from 1 to 4;
n is an integer from 0 to 4;
$R^6$ is hydroxyl, acyloxyl, carboxyl or carboxylate;

$R^4$ and A are as defined above for compounds of formula (I) provided that when A is carbon, m is 1, n is 0, and $R^6$ is hydroxyl occupying site 4 of ring X, then $R^4$ cannot be 4-methoxyphenyl, 4-chlorophenyl, 2-fluorophenyl, 2,4-dichlorophenyl, 2,6-dichlorophenyl or benzyl [Kim, H. R.; Shin, S. I.; Park, H. J.; Jeon, D. J.; Ryu, E. K. *Bull. Korean Chem. Soc.* 1999, 20, 122-124. Adembri, G.; Giorgi, G.; Lampariello, R. L.; Paoli, M. L.; Sega, A. *J. Chem. Soc., Perkin Trans.* 1 2000, 2649-2656., Lakhvich, F. A.; Khripach, V. A.; Pyrko, A. N.; Antonevich, I. P.; Yankova, T. V.; Koroleva, E. V.; Akhrem, A. A. *Khim. Geterotsikl. Soed.* 1988, 972-976.]

when A is carbon, m is 3, n is 0, and $R^6$ is carboxylic acid methyl ester occupying site 6 of ring X, then $R^4$ cannot be 4-chlorophenyl or 4-(1-methylethyl)phenyl [Lawton, G.; Osbond, J. M.; Self, C. R., *Eur. Pat. Appl.* 1991, EP409273A2]

when A is carbon, m is 4, n is 0, and $R^6$ is carboxylic acid methyl ester occupying site 6 or 7 of ring X, then $R^4$ cannot be 4-chlorophenyl [Lawton, G.; Osbond, J. M.; Self, C. R., *Eur. Pat. Appl.* 1991, EP409273A2]

In the compounds of formula (I), $R^1$ is preferably hydrogen or lower alkyl.

$R^2$ is preferably hydrogen, lower alkyl or phenyl.

$R^3$ is preferably benzyl or alkyl which forms an alicyclic structure with R'.

In the compounds of formulae (I) and (II), $R^4$ may be selected from phenyl which is substituted with 1-5 $R^5$, or from naphthalen-1-yl, naphthalen-2-yl, benzyl, phenethyl or 3-phenylpropyl which is substituted with 0-5 $R^5$. Preferably $R^4$ is a phenyl substituted by 1-2 substituents $R^5$.

In the preferred compounds of formula (I), substituents $R^5$ are selected from the group consisting of halogen, nitro, cyano, lower alkyl, hydroxyl and lower alkoxyl. Alkyl or alkoxyl groups may be further substituted by the above mentioned groups.

Even more preferably substituents $R^5$ are halogen, nitro, cyano, lower alkyl or lower haloalkyl groups.

In the preferred compounds of formula (I), $R^4$ is an unsubstituted naphthalen-1-yl, naphthalen-2-yl or benzyl or a phenyl mono- or disubstituted with halogen, nitro, cyano, lower alkyl or haloalkyl groups.

In the context of the present application, the general terms used above and below preferably have the following meanings:

A prodrug is a drug which is administered in an inactive or significantly less active form but once administered, it is metabolised in vivo into the active compound.

Alkyl is a saturated hydrocarbon radical containing 1-20, preferably 1-8 carbon atoms. It is for example methyl, ethyl, n-propyl, isopropyl, n-butyl, isobutyl, sec-butyl, tert-butyl, pentyl, hexyl, heptyl or octyl.

Lower alkyl contains 1-6, preferably 1-4 carbon atoms. It is for example ethyl, methyl, n-propyl, isopropyl, n-butyl, isobutyl, sec-butyl, tert-butyl, pentyl or hexyl, preferably methyl, ethyl, n-propyl or isopropyl.

Haloalkyl group is a saturated hydrocarbon radical containing 1-5 carbon atoms, each substituted with 0-3 fluorine, chlorine, bromine or iodine atoms. Preferably it is a trifluoromethyl group.

In this description lower alkoxy contains 1-6, preferably 1-2 carbon atoms. It is for example methoxy, ethoxy, n-propoxy, isopropoxy, n-butoxy, isobutoxy, secbutoxy, tert-butoxy, pentyloxy or ethyloxy, preferably methoxy.

Monocyclic aliphatic unsubstituted structure contains 3-10, preferable 5-8 carbon atoms. It is for example cyclopentyl, cyclohexyl, cycloheptyl or cyclooctyl ring.

Halogen is fluorine, chlorine, bromine, or iodine, preferably fluorine or chlorine.

The compounds of the invention may contain one or more asymmetric centers and can thus occur as racemates and racemic mixtures, single enantiomers, diastereomeric mixtures and individual diastereomers. The present invention is meant to comprehend all such isomeric forms of the compounds of the invention.

The present invention also includes isotopically-labeled compounds, which are identical to those recited in formula (I) but for the fact that one or more atoms may be replaced by an atom having an atomic mass or mass number different from the atomic mass or mass number usually found in nature. Examples of isotopes that can be incorporated into compounds of the invention include isotopes of hydrogen, carbon, nitrogen, oxygen, fluorine and chlorine, such as $^2$H, $^3$H, $^{13}$C, $^{14}$C, $^{15}$N, $^{18}$O, $^{17}$O, $^{18}$F, and $^{36}$Cl, respectively. Certain isotopically labelled compounds, for example those into which radioactive isotopes such as $^3$H and $^{14}$C are incorporated, are useful in drug and/or substrate tissue distribution assays. Further, substitution with heavier isotopes such as deuterium ($^2$H) can afford certain therapeutic advantages resulting from greater metabolic stability, for example increased in vivo half-life or reduced dosage requirements. Isotopically labelled compounds of the present invention can generally be prepared by carrying out the procedures disclosed in the Schemes and Examples, by substituting a readily available isotopically labelled reagent for a non-isotopically labelled reagent.

The invention relates particularly to the compounds of formula (I)

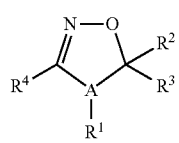

(I)

or stereoisomers, pharmaceutically acceptable salts or prodrug forms thereof, wherein A is carbon or nitrogen, $R^1$ is hydrogen or lower alkyl, $R^2$ is hydrogen, lower alkyl or phenyl, provided that $R^1$ and $R^2$ cannot simultaneously be hydrogen, $R^3$ is selected from alkyl or benzyl and may form a monocyclic aliphatic structure with $R^1$, provided that $R^2$ and $R^3$ cannot simultaneously be alkyl, and $R^4$ is an unsubstituted naphthalen-1-yl, naphthalen-2-yl or benzyl or a phenyl mono- or disubstituted with halogen, nitro, cyano, lower alkyl or haloalkyl groups.

More preferably, the compounds of formula (I) or stereoisomers, pharmaceutically acceptable salts or prodrug forms thereof are those having formula (I) wherein
A is carbon,
$R^1$ forms with $R^3$ a monocyclic aliphatic structure,
$R^2$ is hydrogen, and
$R^4$ is a phenyl mono- or disubstituted with halogen, nitro, cyano, lower alkyl or haloalkyl groups.

Preferred examples of the compounds of the invention are selected from the group consisting of 5-benzyl-3-(3-methoxyphenyl)-5-methyl-4,5-dihydro-isoxazole (2), 5-benzyl-3-(2-fluorophenyl)-5-methyl-4,5-dihydro-isoxazole (4), 5-benzyl-3-naphthalen-2-yl-5-methyl-4,5-dihydro-isoxazole (9), 5-benzyl-3-(2-methoxy-phenyl)-5-phenyl-4,5-dihydro-isoxazole (12), 5-benzyl-3-(4-nitrophenyl)-5-phenyl-4,5-dihydro-isoxazole (17), 4-(5-benzyl-5-phenyl-4,5-dihydro-isoxazol-3-yl)-benzonitrile (18), 3-(4-fluoro-2-trifluoromethyl-phenyl)-4,5,6,6a-tetrahydro-3aH-cyclopenta[d]isoxazole (20), 3-(4-nitro-3-trifluoromethyl-phenyl)-4,5,6,6a-tetrahydro-3aH-cyclopenta[d]isoxazole (21), 3-(4-fluoro-3-trifluoromethyl-phenyl)-3a,4,5,6,7,7a-hexahydro-benzo-[d]-isoxazole (35), 3-(4-fluoro-2-trifluoromethyl-phenyl)-3a,4,5,6,7,7a-hexahydro-benzo[d]-isoxazole (36), 3-(4-nitro-3-trifluoro-methyl-phenyl)-3a,4,5,6,7,7a-hexahydro-benzo[d]isoxazole (37), 3-(4-nitro-2-tri-fluoromethyl-phenyl)-3a,4,5,6,7,7a-hexahydro-benzo[d]isoxazole (38), 3-(4-fluoro-2-trifluoromethyl-phenyl)-4,5,6,7,8,8a-hexahydro-3aH-cyclohepta-[d]-isoxazole (40), 3-(4-nitro-3-trifluoromethyl-phenyl)-4,5,6,7,8,8a-hexahydro-3aH-cyclohepta[d]isoxazole (41), 3-(4-nitro-2-trifluoromethyl-phenyl)-4,5,6,7,8,8a-hexahydro-3aH-cyclohepta[d]isoxazole (42), 3-(4-fluoro-2-trifluoromethyl-phenyl)-3a,4,5,6,7,8,9,9a-octahydro-cycloocta[d]isoxazole (44), 3-(4-nitro-2-trifluoromethyl-phenyl)-3a,4,5,6,7,8,9,9a-octahydro-cycloocta[d]isoxazole (46), 3-Benzyl-3a,4,5,6,7,7a-hexahydro-benzo[d]isoxazole (47), 5-benzyl-4-butyl-3-(3-chloro-phenyl)-5-methyl-4,5-dihydro-[1,2,4]oxadiazole (50), 5-benzyl-4-butyl-5-methyl-3-(4-nitro-phenyl)-4,5-dihydro-[1,2,4]oxadiazole (51), 4-(5-benzyl-4-butyl-5-methyl-4,5-dihydro-[1,2,4]oxadiazol-3-yl)-benzonitrile (52), 3,5-dibenzyl-4-butyl-5-methyl-4,5-dihydro-[1,2,4]oxadiazole (55), 4-(5-benzyl-4-isobutyl-5-methyl-4,5-dihydro-[1,2,4]oxadiazol-3-yl)-benzonitrile (62), 4-(4,5,6,6a-tetrahydro-3aH-cyclopenta[d]isoxazol-3-yl)-2-trifluoromethyl-benzonitrile (85), 4-(4,5,6,6a-tetrahydro-3aH-cyclopenta[d]isoxazol-3-yl)-3-trifluoromethyl-benzonitrile (86), 4-(3a,4,5,6,7,7a-hexahydro-benzo[d]isoxazol-3-yl)-3-trifluoromethyl-benzonitrile (88), 4-(3a,4,5,6,7,7a-hexahydro-benzo[d]isoxazol-3-yl)-2-trifluoromethyl-benzonitrile (89), 4-(4,5,6,7,8,8a-hexahydro-3aH-cyclohepta[d]isoxazol-3-yl)-3-trifluoro-methyl-benzonitrile (90), 4-(4,5,6,7,8,8a-hexahydro-3aH-cyclohepta[d]isoxazol-3-yl)-2-trifluoro-methyl-benzonitrile (91), 4-(3a,4,5,6,7,8,9,9a-octahydro-cyclo-octa-[d]isoxazol-3-yl)-3-trifluoromethyl-benzonitrile (92), 4-(3a,4,5,6,7,8,9,9a-octa-hydro-cycloocta[d]isoxazol-3-yl)-3-trifluoromethyl-benzonitrile (93).

The invention also relates to pharmaceutical compositions which contain a compound of the formula (I) or (II) or a pharmaceutically acceptable salt thereof as active ingredient. These pharmaceutical compositions are for example those for enteral, such as in particular oral, those for parenteral administration, and those for local administration to warm-blooded animals, in particular to humans.

The pharmaceutical compositions according to the invention usually contain the pharmacologically active ingredient according to formula (I) or (II) together with known pharmaceutical excipients. The amount of the active ingredient in the pharmaceutical compositions according to the invention is, for example, from about 0.001% to 100% by weight, preferably from about 0.1% to about 50% by weight. The dose of the active ingredient can depend on various factors, such as the efficacy of the active ingredient, severity of the disease to be treated or its symptoms, administration procedure, sex, age, weight and/or individual condition of the subject in need of the treatment. In a normal case, for a human adult of about 75 kg in weight, one daily dose of about 1 mg to about 1000 mg, in particular from about 10 mg to about 500 mg, is to be estimated. This can be administered as a single dose or in several sub-doses.

The invention also relates to the compounds of the formula (I) for use in a method for treating disease states, disorders and conditions alleviated by compounds having androgen, antiandrogen or androgen receptor modulator activity. Among such conditions may be mentioned prostate cancer, including primary and hormone refractory prostate cancer, bening prostate hyperplasia, ovarian cancer, breast cancer, hepatocellular carcinoma, alopecia, hirsutism, acne vulgaris, endometriosis, acanthosis nigricans, hypertrichosis, precocious puberty, polycystic ovary syndrome, hypersexuality/paraphilia, sarcopenia, osteoporosis, muscle wasting, wasting disease, cancer cachexia, frailty, menopausal and andropausal vasomotor conditions, urinary incontinence, sexual dysfunction, erectile dysfunction, depression, uterine fibroid disease, male contraception and impotence. In addition, the compounds of the formula (I) and (II) may be used as female and male hormone replacement therapy, as stimulant of hematopoiesis, and as an anabolic agent.

The invention also provides a method for the therapeutic or prophylactic treatment of disease states, disorders and conditions alleviated by compounds having androgen, antiandrogen or androgen receptor modulator activity, said method comprising administering an effective amount of a compound of formula (I) or (II) as defined above to a subject in need of such treatment.

A still further object of the invention is a method for the therapeutic or prophylactic treatment of prostate cancer, bening prostate hyperplasia, ovarian cancer, breast cancer, hepatocellular carcinoma, alopecia, hirsutism, acne vulgaris, endometriosis, acanthosis nigricans, hypertrichosis, precocious puberty, polycystic ovary syndrome, hypersexuality/paraphilia, sarcopenia, osteoporosis, muscle wasting, wasting disease, cancer cachexia, frailty, menopausal and andropausal vasomotor conditions, urinary incontinence, sexual dysfunction, erectile dysfunction, depression, uterine fibroid disease, male contraception and impotence, said method comprising administering an effective amount of a compound of formula (I) or (II) as defined above to a subject in need of such treatment.

The compounds of the formula (I) and (II) can be prepared as described below. The reagents used in the preparation of the compounds of this invention can be either commercially obtained or can be prepared by standard procedures described in the literature.

Scheme 1.

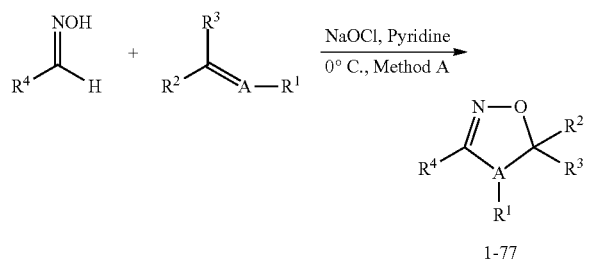

Scheme 2.

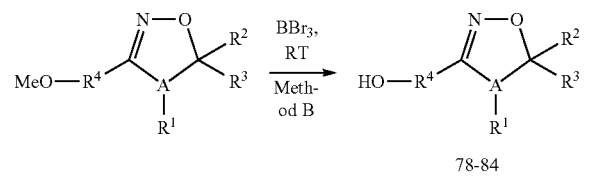

Scheme 3.

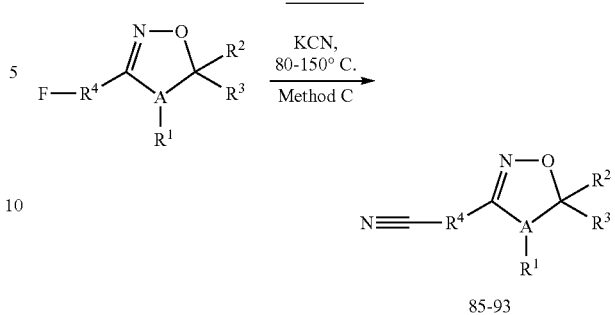

A process for preparing the compounds of the invention thus comprises

Scheme 1 (examples 1-77): nitrile oxide-dipolarophile cycloaddition reaction of an aldoxime comprising $R^4$, wherein $R^4$ is as defined above, with an olefin or imine comprising $R^1$, $R^2$ and $R^3$, wherein $R^1$, $R^2$ and $R^3$ are as defined above, in the presence of sodium hypochlorite and pyridine to afford the desired heterocycles; or Scheme 2 (examples 78-84): demethylation reaction of the appropriate methoxy-substituted compounds in the presence of boron tribromide to afford the desired phenolic products; or Scheme 3 (examples 85-95): cyano-dehalogenation reaction of the appropriate fluoro compounds in the presence of potassium cyanide to afford the desired benzonitrile products.

The invention also relates to the compounds of formula (I)

(I)

or stereoisomers, pharmaceutically acceptable salts or prodrug forms thereof, wherein A is carbon or nitrogen;

$R^1$ is hydrogen or alkyl;

$R^2$ is hydrogen, alkyl or phenyl, provided that $R^1$ and $R^2$ cannot simultaneously be hydrogen;

$R^3$ is alkyl or benzyl and may form with $R^1$ a monocyclic aliphatic structure, which may be substituted with a side chain of the formula

wherein n is an integer from 0 to 4, and $R^6$ is hydroxyl, acyloxyl, carboxyl or carboxylate;

provided that $R^2$ and $R^3$ cannot simultaneously be alkyl;

$R^4$ is phenyl which is substituted with 1-5 $R^5$, or naphthalen-1-yl, naphthalen-2-yl, benzyl, phenethyl or 3-phenylpropyl which is substituted with 0-5 $R^5$;

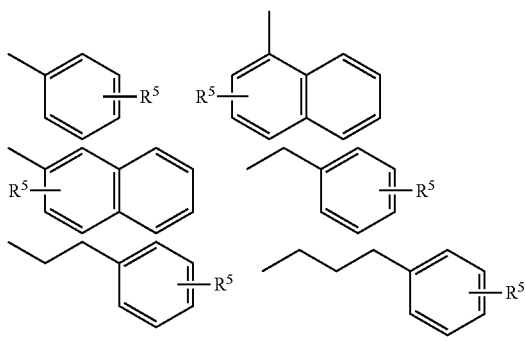

$R^5$ is selected from the group consisting of halogen, nitro, cyano, alkyl, hydroxyl and lower alkoxyl, provided that when $R^4$ is phenyl there can not be more than one hydroxyl or lower alkoxyl simultaneously present as $R^5$, provided that when A is carbon, $R^1$ is hydrogen, $R^2$ is methyl and $R^3$ is benzyl, then $R^4$ cannot be 2-, 3- or 4-methoxyphenyl, 2-fluorophenyl, 2-, 3- or 4-chlorophenyl, 4-benzonitrile, or naphthalene-2-yl [WO2009066009]

when A is carbon, $R^1$ is hydrogen, $R^2$ is phenyl and $R^3$ is benzyl, then $R^4$ cannot be 2-, 3- or 4-methoxyphenyl, 2-fluorophenyl, 4-chlorophenyl or 4-nitrophenyl [WO2009066009]

when A is carbon, $R^1$ is hydrogen, $R^2$ is phenyl and $R^3$ is methyl, then $R^4$ cannot be phenethyl, 3-phenyl-propyl, 2-(2-, 3- or 4-hydroxyphenyl)-ethyl or 3-(4-hydroxyphenyl)propyl [WO2009066009], for use as pharmaceuticals, and for use in a method for treating disease states, disorders or conditions alleviated by compounds having androgen, antiandrogen or androgen receptor modulator activity.

A further object of the invention is a pharmaceutical composition comprising a compound of the formula (I)

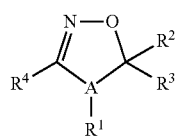

(I)

or a stereoisomer, pharmaceutically acceptable salt or a prodrug form thereof,
wherein
A is carbon or nitrogen;
$R^1$ is hydrogen or alkyl;
$R^2$ is hydrogen, alkyl or phenyl, provided that $R^1$ and $R^2$ cannot simultaneously be hydrogen;
$R^3$ is alkyl or benzyl and may form with $R^1$ a monocyclic aliphatic structure, which may be substituted with a side chain of the formula

wherein n is an integer from 0 to 4, and $R^6$ is hydroxyl, acyloxyl, carboxyl or carboxylate;
provided that $R^2$ and $R^3$ cannot simultaneously be alkyl;
$R^4$ is phenyl which is substituted with 1-5 $R^5$, or naphthalen-1-yl, naphthalen-2-yl, benzyl, phenethyl or 3-phenylpropyl which is substituted with 0-5 $R^5$;

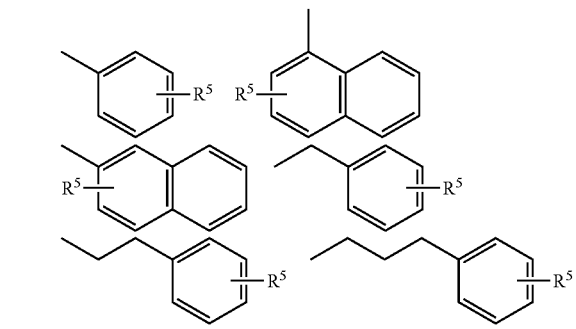

$R^5$ is selected from the group consisting of halogen, nitro, cyano, alkyl, hydroxyl and lower alkoxyl, provided that when $R^4$ is phenyl there can not be more than one hydroxyl or lower alkoxyl simultaneously present as $R^5$ and that alkyl or alkoxyl groups may be further substituted by the above mentioned groups, provided that when A is carbon, $R^1$ is hydrogen, $R^2$ is methyl and $R^3$ is benzyl, then $R^4$ cannot be 2-, 3- or 4-methoxyphenyl, 2-fluorophenyl, 2-, 3- or 4-chlorophenyl, 4-benzonitrile, or naphthalen-2-yl [WO2009066009]

when A is carbon, $R^1$ is hydrogen, $R^2$ is phenyl and $R^3$ is benzyl, then $R^4$ cannot be 2-, 3- or 4-methoxyphenyl, 2-fluorophenyl, 4-chlorophenyl or 4-nitrophenyl [WO2009066009]

when A is carbon, $R^1$ is hydrogen, $R^2$ is phenyl and $R^3$ is methyl, then $R^4$ cannot be phenethyl, 3-phenyl-propyl, 2-(2-, 3- or 4-hydroxyphenyl)-ethyl or 3-(4-hydroxyphenyl)propyl [WO2009066009]

in association with a pharmaceutically acceptable carrier.

The invention also provides a method for treating disease states, disorders or conditions alleviated by compounds having androgen, antiandrogen or androgen receptor modulator activity, said method comprising administering an effective amount of a compound of formula (I)

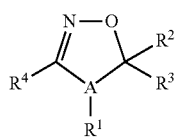

(I)

or stereoisomers, pharmaceutically acceptable salts or prodrug forms thereof,
wherein
A is carbon or nitrogen;
$R^1$ is hydrogen or alkyl;
$R^2$ is hydrogen, alkyl or phenyl, provided that $R^1$ and $R^2$ cannot simultaneously be hydrogen;
$R^3$ is alkyl or benzyl and may form with $R^1$ a monocyclic aliphatic structure, which may be substituted with a side chain of the formula

wherein n is an integer from 0 to 4, and $R^6$ is hydroxyl, acyloxyl, carboxyl or carboxylate;

provided that R² and R³ cannot simultaneously be alkyl;
R⁴ is phenyl which is substituted with 1-5 R⁵, or naphthalene-1-yl, naphthalene-2-yl, benzyl, phenethyl or 3-phenylpropyl which is substituted with 0-5 R⁵;

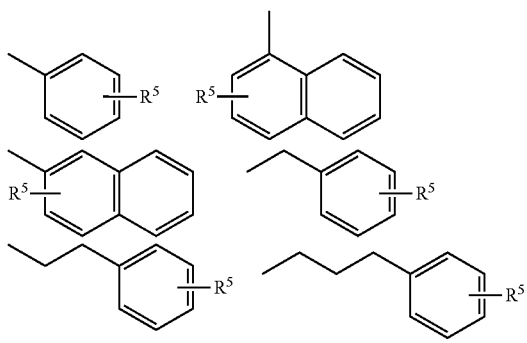

R⁵ is selected from the group consisting of halogen, nitro, cyano, alkyl, hydroxyl and lower alkoxyl, provided that when R⁴ is phenyl there can not be more than one hydroxyl or lower alkoxyl simultaneously present as R⁵ and that alkyl or alkoxyl groups may be further substituted by the above mentioned groups;
to a subject in need of such treatment.

Figure 1:
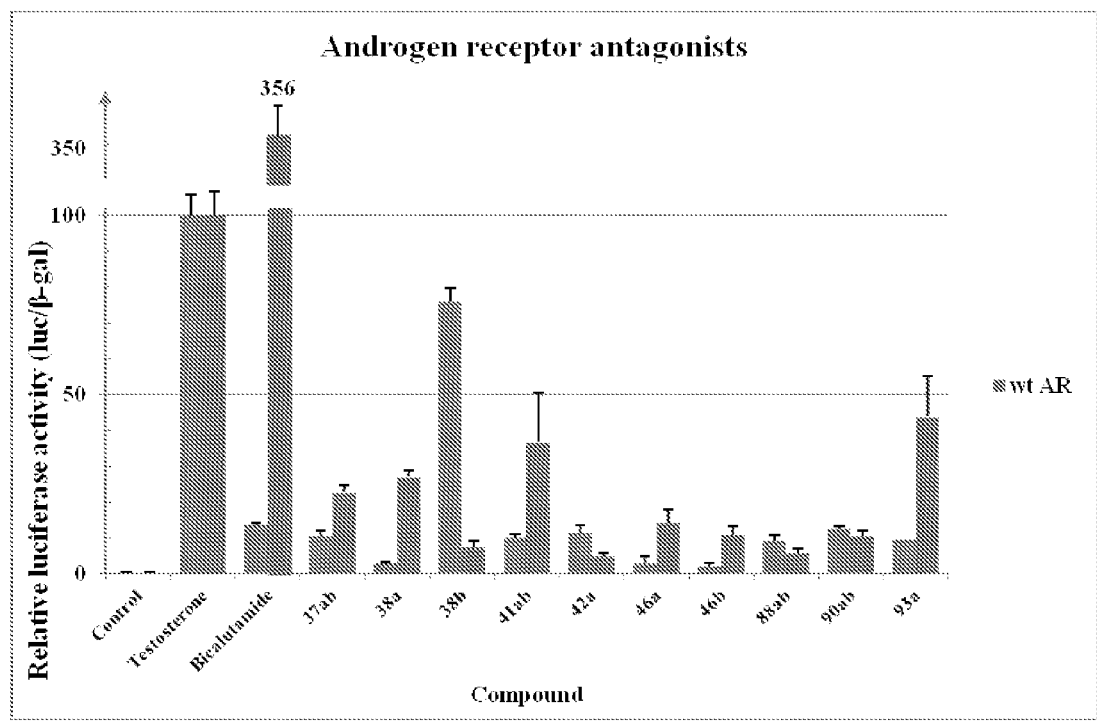
FIG. 1 shows inhibition of transcriptional activation of wild type and W741L-mutated AR in COS-1 cells in the presence of the ten most efficient compounds of the present invention. (W741L is common in patients with hormone responsive prostate cancer. It turns bicalutamide to an AR-agonist).

The following examples further illustrate the invention described above. Compounds 1-4, 7-13, 15-16 and 81-84 have been disclosed in WO 2009/066009 and are not claimed as such in the present application.

EXAMPLES 1-77

5-Benzyl-3-(2-methoxyphenyl)-5-methyl-4,5-dihydro-isoxazole (1)

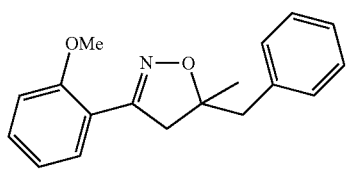 [SMILES: COc1ccccc1C1=NOC(C)(Cc2ccccc2)C1]

Method A:

2-Methoxybenzaldehyde oxime (1.95 g, 0.0129 mol) is dissolved into 100 ml of chloroform. (2-Methyl-allyl)-benzene (2.56 g, 0.0194 mol) and pyridine (0.31 g, 0.0039 mol) are then added and the solution is cooled to 0° C. After that, 5% NaOCl solution (58 ml, 0.039 mol) is added dropwise to the vigorously stirred reaction mixture keeping the temperature of the solution at 0-5° C. for 1.5 h. Then the mixture is allowed to warm to the room temperature. The organic layer is separated and the water phase extracted with dichloromethane. The combined organic phase is then washed with 2 M HCl, saturated NaHCO₃ and water, dried with MgSO₄ and evaporated to dryness. The residue is purified by column chromatography using dichloromethane as an eluent.

Yield 45%, a brown viscous, ¹H NMR δ 7.58 (dd, 1H, J=7.7, 1.8), 7.31 (m, 1H), 7.28-7.25 (m, 4H), 7.20 (m, 1H), 6.91 (ddd, 1H, J=7.6, 7.6, 1.0), 6.87 (d, 1H, J=8.4), 3.78 (s, 3H), 3.33 (d, 1H, J=17.2), 3.09 (d, 1H, J=17.2), 2.97 (s, 2H), 1.42 (s, 3H); ¹³C NMR δ 157.4, 156.2, 137.0 (3 s), 130.9, 130.4, 129.2, 128.1, 126.5, 120.7 (6 d), 119.4 (s), 111.3, 87.0 (2 d), 55.4 (q), 47.3, 45.7 (2 t), 25.4 (q). [WO2009066009, compound 51]

The following compounds were prepared by Method A using appropriate starting materials:

5-Benzyl-3-(3-methoxyphenyl)-5-methyl-4,5-dihydro-isoxazole (2)

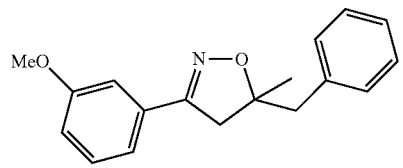 [SMILES: COc1cccc(C2=NOC(C)(Cc3ccccc3)C2)c1]

Yield 56%, a brown viscous oil, ¹H NMR δ 7.28-7.19 (m, 7H), 7.09 (d, 1H, J=7.7), 6.90 (dd, 1H, J=8.2, 2.1), 3.78 (s, 3H), 3.18 (d, 1H, J=16.5), 2.99 (s, 2H), 2.91 (d, 1H, J=16.5), 1.43 (s, 3H); ¹³C NMR δ 159.6, 156.4, 136.7, 131.4 (4 s), 130.3, 129.6, 128.2, 126.7, 119.1, 116.1, 111.0, 87.5 (8 d), 55.3 (q), 45.6, 44.5 (2 t), 25.8 (q). [WO2009066009, compound 52]

5-Benzyl-3-(4-methoxyphenyl)-5-methyl-4,5-dihydro-isoxazole (3)

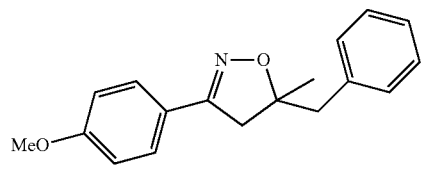 [SMILES: COc1ccc(C2=NOC(C)(Cc3ccccc3)C2)cc1]

Yield 37%, mp=97.8-98.6° C.; ¹H NMR δ 7.53 (m, 2H), 7.29-7.27 (m, 4H), 7.22 (m, 1H), 6.88 (m, 2H), 3.80 (s, 3H), 3.20 (d, 1H, J=16.4), 2.94 (s, 2H), 2.92 (d, 1H, J=16.4), 1.43 (s, 3H); ¹³C NMR δ 160.6, 156.0, 136.9 (3 s), 130.4, 128.2, 127.9, 126.7 (4 d), 122.7 (s), 114.0, 87.0 (2 d), 55.3 (q), 45.7, 44.8 (2 t), 25.7 (q). [WO2009066009, compound 53]

5-Benzyl-3-(2-fluorophenyl)-5-methyl-4,5-dihydro-isoxazole (4)

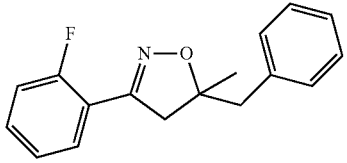

Yield 42%, a pale yellow wax, $^1$H NMR δ 7.74 (ddd, J=7.7, 7.7, 1.7), 7.33 (m, 1H), 7.29-7.27 (m, 4H), 7.23 (m, 1H), 7.12 (ddd, J=7.6, 7.6, 1.1), 7.04 (ddd, J=11.3, 8.4, 0.9), 3.32 (dd, 1H, J=17.2, 2.4), 3.07 (dd, 1H, J=17.2, 2.6), 3.01 (d, 1H, J=14.3), 3.00 (d, 1H, J=14.3), 1.45 (s, 3H); $^{13}$C NMR δ 160.2, 153.2 (2 d), 136.7 (s), 131.4 (dd), 130.4 (d), 128.8 (dd), 128.2, 126.7 (2 d), 124.3 (dd), 118.2 (d), 116.3 (dd), 87.6 (d), 46.4 (td), 45.7 (t), 25.7 (q). [WO2009066009, compound 54]

5-Benzyl-3-(2-chlorophenyl)-5-methyl-4,5-dihydroisoxazole (5)

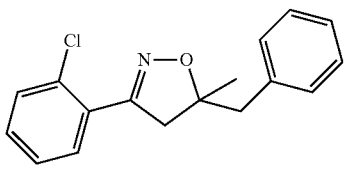 [SMILES: CC1(Cc2ccccc2)CC(c2ccccc2Cl)=NO1]

Yield 50%, a yellow viscous oil, $^1$H NMR δ 7.37 (dd, 1H, J=7.6, 1.7), 7.34 (dd, 1H, J=7.9, 1.3), 7.30-7.17 (m, 7H), 3.33 (d, 1H, J=17.0), 3.15 (d, 1H, J=17.0), 3.02 (dd, 1H, J=13.8), 2.97 (d, 1H, J=13.8), 1.46 (s, 3H); $^{13}$C NMR δ 156.3, 136.7, 132.7 (3 s), 130.5, 130.4, 130.4, 130.2 (4 d), 129.7 (s), 128.2, 126.8, 126.7 (3d), 88.1 (s), 47.0, 45.7 (2 t), 25.7 (q).

5-Benzyl-3-(3-chlorophenyl)-5-methyl-4,5-dihydroisoxazole (6)

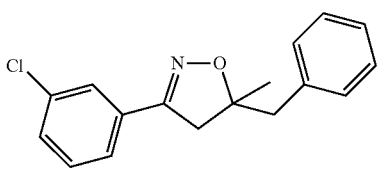 [SMILES: CC1(Cc2ccccc2)CC(c2cccc(Cl)c2)=NO1]

Yield 52%, a yellow viscous oil, $^1$H NMR δ 7.55 (dd, 1H, J=1.7, 1.6), 7.45 (ddd, 1H, J=7.5, 1.7, 1.6), 7.31-7.23 (m, 6H), 7.21 (m, 1H), 3.17 (d, 1H, J=16.5), 3.00 (d, 1H, J=14.1), 3.00 (d, 1H, J=14.1), 2.89 (dd, 1H, J=14.1), 1.44 (s, 3H); $^{13}$C NMR δ 155.3, 136.5, 134.6, 131.9 (4 s), 131.9, 129.8, 129.6, 128.3, 126.8, 126.4, 124.4 (7 d), 87.9 (s), 45.7, 44.2 (2 t), 25.9 (q).

5-Benzyl-3-(4-chlorophenyl)-5-methyl-4,5-dihydro-isoxazole (7)

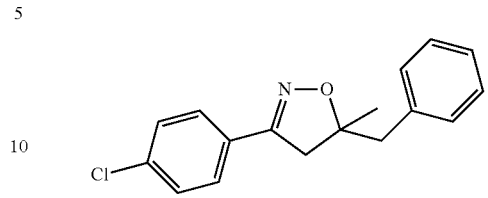

Yield 35%, a pale brown viscous oil, $^1$H NMR δ 7.50 (m, 2H), 7.32 (m, 2H), 7.29-7.26 (m, 4H), 7.23 (m, 1H), 3.18 (d, 1H, J=16.5), 3.01 (d, 1H, J=13.9), 3.00 (d, 1H, J=13.9), 2.91 (d, 1H, J=16.5), 1.45 (s, 3H); $^{13}$C NMR δ 155.4, 136.6, 135.7 (3 s), 130.3, 128.8 (2 d), 128.6 (s), 128.3, 127.6, 126.8, 87.8 (4 d), 45.7, 44.3 (2 t), 25.9 (q). [WO2009066009, compound 55]

4-(5-Benzyl-5-methyl-4,5-dihydro-isoxazol-3-yl)-benzonitrile (8)

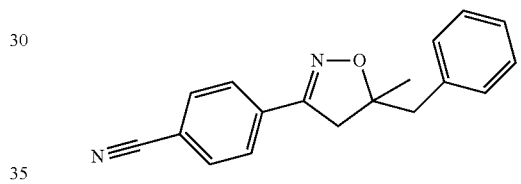

Yield 35%, a pale yellow wax, $^1$H NMR δ 7.67 (m, 2H), 7.63 (m, 2H), 7.29-7.25 (m, 4 OH), 7.22 (m, 1H), 3.20 (d, 1H, J=16.5), 3.05 (d, 1H, J=13.9), 3.00 (d, 1H, J=13.9), 2.94 (d, 1H, J=16.5), 1.48 (s, 3H); $^{13}$C NMR δ 155.0, 136.3, 134.4 (3 s), 132.4, 130.3, 128.3 (3 d), 127.8 (s), 126.9, 126.8 (2 d), 118.4 (s), 88.8 (d), 45.7, 43.7 (2 t), 26.0 (q). [WO2009066009, compound 56]

5-Benzyl-3-naphthalen-2-yl-5-methyl-4,5-dihydro-isoxazole (9)

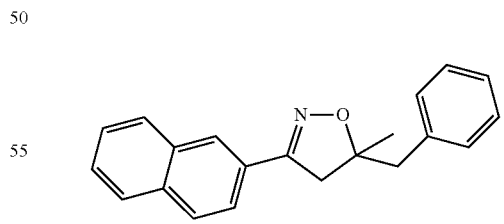

Yield 40%, mp=144.8-146.3° C.; $^1$H NMR δ 7.92 (dd, 1H, J=8.7, 1.5), 7.82-7.78 (m, 4H), 7.49 (m, 2H), 7.38-7.27 (m, 4H), 7.22 (m, 1H), 3.35 (d, 1H, J=16.3), 3.07 (d, 1H, J=16.3), 3.06 (s, 2H), 1.49 (s, 3H); $^{13}$C NMR δ 156.6, 136.8, 133.9, 133.0 (4 s), 130.4, 128.4, 128.3, 128.3, 127.8 (5 d), 127.8 (s), 126.9, 126.8, 126.6, 126.5, 123.4, 87.7 (6 d), 45.8, 44.4 (2 t), 25.9 (q). [WO2009066009, compound 57]

5-Methyl-3-phenethyl-5-phenyl-4,5-dihydroisoxazole (10)

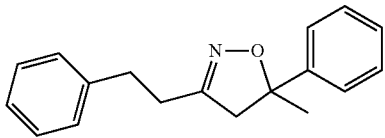 [SMILES: CC1(c2ccccc2)CC(CCc2ccccc2)=NO1]

Yield 65%, yellow viscous oil, $^1$H NMR δ 7.39-7.36 (m, 2H), 7.33 (m, 2H), 7.24 (m, 3H), 7.19-7.16 (1H), 7.15-7.12 (2H), 3.01 (d, 1H, J=16.8), 2.96 (d, 1H, J=16.8), 2.87 (t, 2H, J=8.0), 2.62 (t, 2H, J=8.0), 1.65 (s, 3H); $^{13}$C NMR δ 158.0, 145.8, 140.5 (3 s), 128.5, 128.4, 128.3, 127.2, 126.3, 124.7 (6 d), 86.8 (s), 51.0, 32.7, 29.7 (3 t), 28.1 (q). [WO2009066009, compound 71]

5-Methyl-5-phenyl-3-(3-phenyl-propyl)-4,5-dihydro-isoxazole (11)

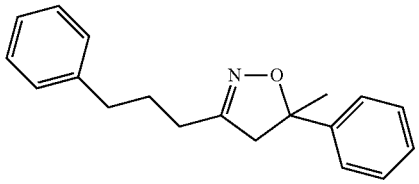 [SMILES: CC1(c2ccccc2)CC(CCCc2ccccc2)=NO1]

Yield 34%, yellow viscous oil, $^1$H NMR δ 7.40 (m, 2H), 7.32 (m, 2H), 7.24 (m, 3H), 7.17 (m, 1H), 7.10 (m, 2H), 3.03 (d, 1H, J=16.7), 2.99 (d, 1H, J=16.7), 2.58 (m, 2H), 2.31 (t, 2H, J=7.5), 1.84 (m, 2H), 1.68 (s, 3H); $^{13}$C NMR δ 158.5, 145.8, 141.4 (3 s), 128.4, 128.4, 128.4, 127.2, 125.9, 124.6 (6 d), 86.6 (s), 50.7, 35.1 (2 t), 28.1 (q), 27.9, 27.4 (2 t). [Arai, N.; Iwakoshi, M.; Tanabe, K.; Narasaka, K. *Bull. Chem. Soc. Jpn.* 1999, 72, 2277-2285], [WO2009066009, compound 115].

5-Benzyl-3-(2-methoxyphenyl)-5-phenyl-4,5-dihydro-isoxazole (12)

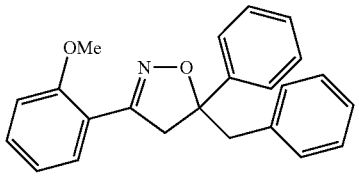 [SMILES: COc1ccccc1C1=NOC(Cc2ccccc2)(c2ccccc2)C1]

Yield 72%, mp=109.3-110.2° C., $^1$H NMR δ 7.54 (dd, 1H, J=7.7, 1.7), 7.37 (m, 2H), 7.32-7.29 (m, 3H), 7.24 (m, 1H), 7.20-7.15 8m, 3H), 7.08 (m, 2H), 6.90 (ddd, 1H, J=7.5, 7.5, 1.0), 6.86 (d, 1H, J=8.4), 3.78 (s, 3H), 3.69 (d, 1H, J=17.1), 3.59 (d, 1H, J=17.1), 3.27 (d, 1H, J=13.8), 3.23 (d, 1H, J=13.8); $^{13}$C NMR δ 157.4, 156.2, 144.6, 136.2 (4 s), 131.1, 130.7, 129.3, 128.1, 127.8, 127.1, 126.5, 125.5, 120.7 (8 d), 119.1 (s), 111.3 (d), 90.6 (s), 55.5 (q), 48.0, 47.4 (2 t). [WO2009066009, compound 74]

5-Benzyl-5-phenyl-3-(3-methoxyphenyl)-4,5-dihydro-isoxazole (13)

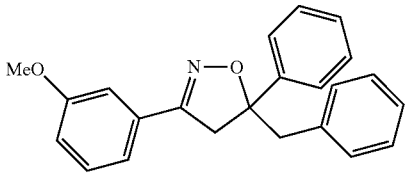 [SMILES: COc1cccc(C2=NOC(Cc3ccccc3)(c3ccccc3)C2)c1]

Yield 66%, mp=94.4-95.2° C., $^1$H NMR δ 7.37 (m, 2H), 7.28 (m, 2H), 7.23-7.12 (m, 6H), 7.09-7.03 (m, 3H), 6.85 (d, 1H, J=7.5), 3.72 (s, 3H), 3.52 (d, 1H, J=16.4), 3.43 (d, 1H, J=16.4), 3.28 (d, 1H, J=13.9), 3.23 (d, 1H, J=13.9); $^{13}$C NMR δ 159.6, 156.5, 144.3, 135.8, 130.9 (5 s), 130.6, 129.5, 128.2, 127.9, 127.3, 126.7, 125.3, 119.1, 116.2, 111.0 (10 d), 90.9 (s), 55.4 (q), 47.3, 45.4 (2 t). [WO2009066009, compound 77]

5-Benzyl-3-(4-methoxyphenyl)-5-phenyl-4,5-dihydro-isoxazole (14)

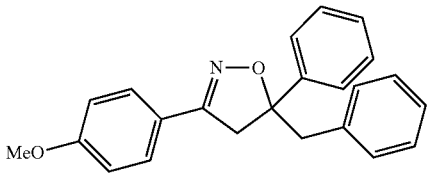

Yield 63%, mp=139.3-141.0° C., $^1$H NMR δ 7.50 (m, 2H), 7.37 (m, 2H), 7.30 (m, 2H), 7.22 (m, 1H), 7.19-7.12 (m, 3H), 7.08 (m, 2H), 6.83 (m, 2H), 3.75 (s, 3H), 3.53 (d, 1H, J=16.3), 3.42 (d, 1H, J=16.3), 3.29 (d, 1H, J=14.0), 3.23 (d, 1H, J=14.0); $^{13}$C NMR δ 160.9, 156.1, 144.5, 136.0 (4 s), 130.7, 128.2, 128.0, 127.9, 127.4, 126.6, 125.4 (7 d), 122.3 (s), 114.4 (d), 90.5 (s), 55.3 (q), 47.3, 45.6 (2 t).

5-Benzyl-3-(2-fluorophenyl)-5-phenyl-4,5-dihydro-isoxazole (15)

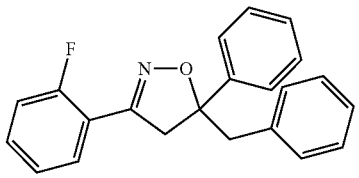 [SMILES: Fc1ccccc1C1=NOC(Cc2ccccc2)(c2ccccc2)C1]

Yield 56%, mp=134.3-135.2° C., $^1$H NMR δ 7.72 (ddd, 1H, J=7.7, 7.6, 1.7), 7.38 (m, 2H), 7.35-7.29 (m, 3H), 7.26 (dd, 1H, J=7.3, 7.1), 7.21-7.15 (m, 3H), 7.10 (m, 2H), 7.09 (dd, J=7.3, 1.0), 7.03 (ddd, 1H, J=10.6, 8.4, 0.8), 3.67 (dd, 1H, J=17.1, 2.4), 3.58 (dd, 1H, J=17.1, 2.5), 3.31 (d, 1H, J=13.9), 3.24 (d, 1H, J=13.9); $^{13}$C NMR δ 160.2, 153.3 (2 d), 144.3, 135.8 (2 s), 131.6 (dd), 130.7 (d), 128.8 (dd), 128.3, 127.9, 127.4, 126.7, 125.4, 124.3 (6 d), 117.8 (d), 116.3 (dd), 91.1 (s), 47.4 (t), 47.1 (td). [WO2009066009, compound 75]

5-Benzyl-3-(4-chlorophenyl)-5-phenyl-4,5-dihydro-isoxazole (16)

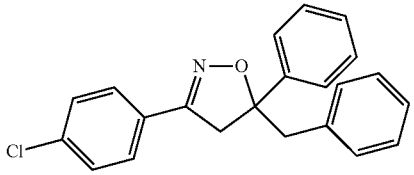 [SMILES: Clc1ccc(C2=NOC(Cc3ccccc3)(c3ccccc3)C2)cc1]

Yield 40%, mp=120.3-122.1° C.; $^1$H NMR δ 7.49 (m, 2H), 7.39 (m, 2H), 7.33 (m, 2H), 7.27 (m, 1H), 7.21-7.15 (m, 3H), 7.10 (m, 2H), 3.54 (d, 1H, J=16.4), 3.45 (d, 1H, J=16.4), 3.32 (d, 1H, J=14.0), 3.25 (d, 1H, J=14.0); $^{13}$C NMR δ 155.5, 144.2, 135.8, 135.7 (4 s), 130.6, 128.8, 128.3 (3 d), 128.2 (s), 128.0, 127.7, 127.4, 126.8, 125.3 (5 d), 91.2 (s), 47.4, 45.2 (2 t). [WO2009066009, compound 76]

5-Benzyl-3-(4-nitrophenyl)-5-phenyl-4,5-dihydro-isoxazole (17)

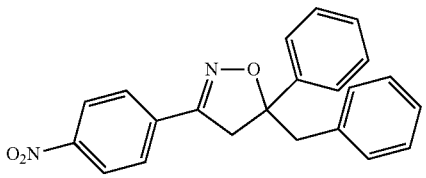 [SMILES: O=[N+]([O-])c1ccc(C2=NOC(Cc3ccccc3)(c3ccccc3)C2)cc1]

Yield 13%, mp=158.0-159.2° C.; $^1$H NMR δ 8.15 (m, 2H), 7.70 (m, 2H), 7.39 (m, 2H), 7.35 (m, 2H), 7.28 (m, 1H), 7.23-7.15 (m, 3H), 7.12 (m, 2H), 3.59 (d, 1H, J=16.5), 3.49 (d, 1H, J=16.5), 3.35 (d, 1H, J=14.1), 3.26 (d, 1H, J=14.1); $^{13}$C NMR δ 155.4, 148.8, 144.4, 136.2, 135.9 (5 s), 131.1, 128.9, 128.6, 128.1, 127.6, 127.4, 125.6, 124.3 (8 d), 92.8 (s), 48.0, 45.2 (2 t).

4-(5-Benzyl-5-phenyl-4,5-dihydro-isoxazol-3-yl)-benzonitrile (18)

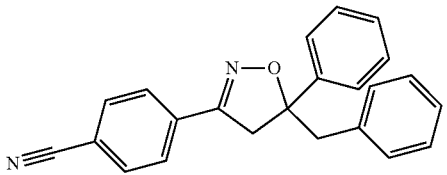 [SMILES: N#Cc1ccc(C2=NOC(Cc3ccccc3)(c3ccccc3)C2)cc1]

Yield 33%, mp=104.5-107.0° C.; $^1$H NMR δ 7.63 (m, 2H), 7.59 (m, 2H), 7.38 (m, 2H), 7.34 (m, 2H), 7.26 (m, 1H), 7.22-7.16 (m, 3H), 7.11 (m, 2H), 3.55 (d, 1H, J=16.5), 3.45 (d, 1H, J=16.5), 3.34 (d, 1H, J=14.1), 3.24 (d, 1H, J=14.1); $^{13}$C NMR δ 155.6, 144.4, 135.9, 134.4, 133.2 (5 s), 132.8, 131.1, 128.9, 128.5, 128.1, 127.3, 125.6 (7 d), 118.8 (s), 113.6 (d), 92.5 (s), 47.9, 45.1 (2 t).

3-(4-Fluoro-3-trifluoromethyl-phenyl)-4,5,6,6a-tetrahydro-3aH-cyclopenta[d]-isoxazole (19)

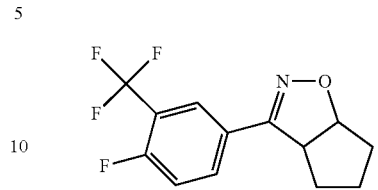

Yield 70%, a yellow wax; $^1$H NMR δ 7.94 (d, 1H, J=7.0), 7.88 (m, 1H), 7.24 (m, 1H), 4.28 (dd, 1H, J=8.5, 5.0), 4.03 (m, 1H), 2.19 (m, 1H), 1.95-1.87 (m, 2H), 1.85-1.73 (m, 2H), 1.53 (m, 1H); $^{13}$C NMR δ 160.7 (dd), 157.0 (s), 132.6 (dd), 126.6 (d), 126.0 (qd), 122.6 (q), 119.1 (qd), 117.8 (dd), 88.9, 52.1 (2 d), 36.1, 31.7, 23.8 (3 t).

SL-060709-2: 3-(4-Fluoro-2-trifluoromethyl-phenyl)-4,5,6,6a-tetrahydro-3aH-cyclopenta[d]isoxazole (20)

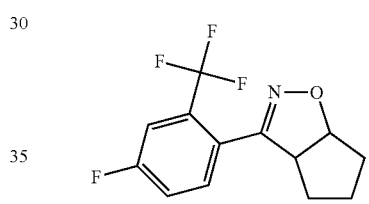

Yield 75%, a yellow wax; $^1$H NMR δ 7.43-7.38 (m, 2H), 7.24 (m, 1H), 5.20 (m, 1H), 4.02 (m, 1H), 2.11 (m, 1H), 1.72-1.65 (m, 2H), 1.64-1.57 (m, 2H), 1.47 (m, 1H); $^{13}$C NMR δ 163.0 (dd), 157.2 (s), 133.9 (dd), 131.3 (qd), 125.3 (d), 123.3 (qd), 119.4 (dd), 115.0 (ddq), 87.9, 55.7 (2 d), 36.2, 30.7, 23.4 (3 t).

SL-210709-1: 3-(4-Nitro-3-trifluoromethyl-phenyl)-4,5,6,6a-tetrahydro-3aH-cyclopenta[d]isoxazole (21)

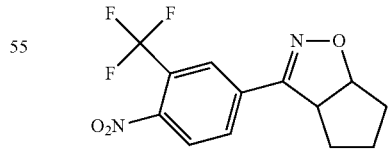

Yield 16%, a yellow wax; $^1$H NMR δ 8.13 (d, 1H, J=1.6), 7.95 (dd, 1H, J=8.5, 1.6), 7.90 (d, 1H, J=8.5), 5.32 (m, 1H), 4.01 (m, 1H), 2.19 (m, 1H), 1.97-1.83 (m, 2H), 1.82-1.75 (m, 2H), 1.50 (m, 1H); $^{13}$C NMR δ 156.5, 148.2, 134.8 (3 s), 131.0 (d), 126.5 (q), 126.1 (d), 124.8 (dq), 122.1 (q), 90.0, 51.4 (2 d), 36.1, 31.8, 23.9 (3 t).

SL-170809-1: 3-(4-Nitro-2-trifluoromethyl-phenyl)-4,5,6,6a-tetrahydro-3aH-cyclopenta[d]isoxazole (22)

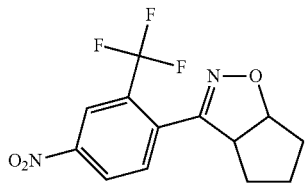 [SMILES: O=[N+]([O-])c1ccc(C2=NOC3CCCC23)c(C(F)(F)F)c1]

Yield 13%, yellow viscous oil $^1$H NMR δ 8.61 (d, 1H, J=2.2), 8.41 (dd, 1H, J=8.5, 2.2), 7.70 (d, 1H, J=8.5), 5.31 (dd, 1H, J=8.9, 5.6), 4.13 (dd, 1H, J=8.9, 8.4), 2.19 (dd, 1H, J=12.2, 6.8), 1.70-1.45 (m, 5H).

3-(2-Methoxy-phenyl)-3a,4,5,6,7,7a-hexahydro-benzo[d]isoxazole (23)

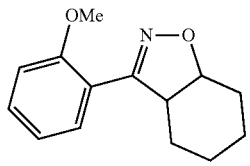 [SMILES: COc1ccccc1C1=NOC2CCCCC12]

Yield 21%, a yellow wax; $^1$H NMR δ 7.61 (dd, 1H, J=7.6, 1.6), 7.34 (ddd, 1H, J=8.4, 7.5, 1.8), 6.94 (ddd, 1H, J=7.6, 7.5, 1.0), 6.90 (dd, 1H, J=8.4), 4.52 (m, 1H), 3.81 (s, 3H), 3.58 (m, 1H), 2.02 (m, 1H), 1.77 (m, 1H), 1.72 (m, 1H), 1.53-1.41 (m, 3H), 1.29-1.18 (m, 2H); $^{13}$C NMR δ 163.5, 157.9 (2 s), 131.6, 130.5, 121.2 (3 d), 119.1 (s), 111.7, 80.3 (2 d), 55.9 (q), 47.1 (d), 26.2, 25.5, 22.6, 20.8 (4 t).

3-(3-Methoxy-phenyl)-3a,4,5,6,7,7a-hexahydro-benzo[d]isoxazole (24)

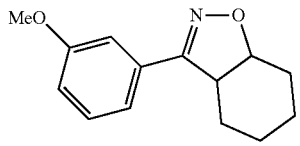 [SMILES: COc1cccc(C2=NOC3CCCCC23)c1]

Yield 77%, a yellow wax; $^1$H NMR δ 7.29 (m, 1H), 7.27 (d, 1H, J=7.9), 7.20 (d, 1H, J=7.7), 6.92 (d, 1H, J=8.2), 4.47 (m, 1H), 3.81 (s, 3H), 3.21 (m, 1H), 2.24 (m, 1H), 1.96 (m, 1H), 1.73 (m, 1H), 1.65 (m, 1H), 1.59 (m, 1H), 1.51 (m, 1H), 1.30-1.18 (m, 2H); $^{13}$C NMR δ 164.3, 160.2, 131.1 (3 s), 130.1, 120.0, 116.7, 111.9, 80.9 (5 d), 55.8 (q), 45.0 (d), 26.9, 25.5, 22.8, 20.6 (4 t).

3-(4-Methoxy-phenyl)-3a,4,5,6,7,7a-hexahydro-benzo[d]isoxazole (25)

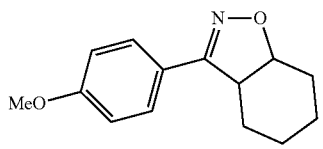 [SMILES: COc1ccc(C2=NOC3CCCCC23)cc1]

Yield 22%, a yellow wax; $^1$H NMR δ 7.61 (m, 2H), 6.89 (m, 2H), 4.43 (m, 1H), 3.80 (s, 3H), 3.19 (m, 1H), 2.23 (m, 1H), 1.93 (m, 1H), 1.72 (m, 1H), 1.67 (m, 1H), 1.58 (m, 1H), 1.51 (m, 1H), 1.25-1.18 (m, 2H); $^{13}$C NMR δ 164.0, 161.4 (2 s), 128.8 (d), 122.4 (s), 114.6, 80.5 (2 d), 55.7 (q), 45.1 (d), 26.9, 25.5, 22.9, 20.7 (4 t).

4-(3a,4,5,6,7,7a-Hexahydro-benzo[d]isoxazol-3-yl)-phenol (26)

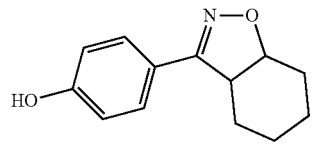 [SMILES: Oc1ccc(C2=NOC3CCCCC23)cc1]

Yield 22%, a yellow wax; $^1$H NMR δ 7.58 (m, 2H), 6.83 (m, 2H), 4.44 (m, 1H), 3.19 (m, 1H), 2.22 (m, 1H), 1.93 (m, 1H), 1.71 (m, 1H), 1.66 (m, 1H), 1.58 (m, 1H), 1.51 (m, 1H), 1.25-1.18 (m, 2H); $^{13}$C NMR δ 164.0, 161.2 (2 s), 129.1 (d), 122.4 (s), 116.1, 80.5 (2 d), 45.1 (d), 26.9, 25.5, 22.9, 20.7 (4 t).

3-(2-Fluoro-phenyl)-3a,4,5,6,7,7a-hexahydro-benzo[d]-isoxazole (27)

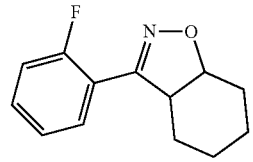 [SMILES: Fc1ccccc1C1=NOC2CCCCC12]

Yield 25%, a yellow viscous oil; $^1$H NMR δ 7.85 (ddd, 1H, J=7.6, 7.5, 1.7), 7.38 (m, 1H), 7.17 (ddd, 1H, J=7.6, 7.5, 0.9), 7.11 (dd, 1H, J=11.3, 8.4), 4.54 (m, 1H), 3.44 (m, 1H), 2.19 (m, 1H), 1.90 (m, 1H), 1.78 (m, 1H), 1.64-1.55 (m, 2H), 1.54 (m, 1H), 1.30-1.20 (m, 2H); $^{13}$C NMR δ 160.9, 160.7 (2 d), 132.0, 129.9, 124.9 (3 dd), 118.0 (d), 116.8 (dd), 80.9, 46.3 (2 d), 25.9, 25.6, 22.5, 20.6 (4 t).

3-(3-Fluoro-phenyl)-3a,4,5,6,7,7a-hexahydro-benzo[d]-isoxazole (28)

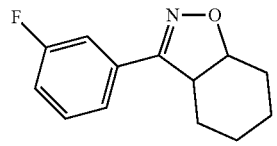 [SMILES: Fc1cccc(C2=NOC3CCCCC23)c1]

Yield 11%, a yellow wax; $^1$H NMR δ 7.47 (d, 1H, J=7.9), 7.43 (m, 1H), 7.37 (m, 1H), 7.09 (m, 1H), 4.52 (m, 1H), 3.23 (m, 1H), 2.27 (m, 1H), 1.98 (m, 1H), 1.77 (m, 1H), 1.72-1.61 (m, 2H), 1.55 (m, 1H), 1.30-1.20 (m, 2H); $^{13}$C NMR δ 163.5, 163.3, 132.0 (3 d), 130.6, 123.0, 117.2, 114.1 (4 dd), 81.1, 44.8 (2 d), 26.8, 25.4, 22.6, 20.5 (4 t).

3-(4-Fluoro-phenyl)-3a,4,5,6,7,7a-hexahydro-benzo[d]-isoxazole (29)

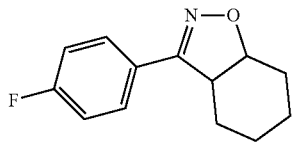 [SMILES: Fc1ccc(C2=NOC3CCCCC23)cc1]

Yield 11%, a yellow wax; $^1$H NMR δ 7.70 (m, 2H), 7.09 (m, 2H), 4.50 (m, 1H), 3.23 (m, 1H), 2.26 (m, 1H), 1.96 (m, 1H), 1.77 (m, 1H), 1.71-1.60 (m, 2H), 1.54 (m, 1H), 1.30-1.20 (m, 2H); $^{13}$C NMR δ 164.1 (d), 163.1 (s), 129.2 (dd), 126.1 (d), 116.3 (dd), 80.9, 45.0 (2 d), 26.8, 25.4, 22.7, 20.6 (4 t).

3-(2-Chloro-phenyl)-3a,4,5,6,7,7a-hexahydro-benzo[d]-isoxazole (30)

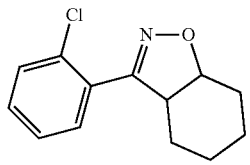 [SMILES: Clc1ccccc1C1=NOC2CCCCC12]

Yield 24%, a colorless wax; $^1$H NMR δ 7.53 (dd, 1H, J=7.6, 1.8), 7.43 (dd, 1H, J=8.1, 1.2), 7.35 (ddd, 1H, J=8.1, 7.5, 1.8), 7.30 (dd, 1H, J=7.6, 7.5, 1.2), 4.67 (m, 1H), 3.70 (m, 1H), 2.04 (m, 1H), 1.83 (m, 1H), 1.71 (m, 1H), 1.57 (m, 1H), 1.59-1.43 (m, 2H), 1.35 (m, 1H), 1.26 (m, 1H); $^{13}$C NMR δ 163.6, 133.5 (2 s), 131.5, 131.2, 130.6 (3 d), 129.5 (s), 127.3 (d), 80.6, 47.2 (2 d), 26.2, 25.2, 22.4, 20.7 (4 t).

3-(3-Chloro-phenyl)-3a,4,5,6,7,7a-hexahydro-benzo[d]-isoxazole (31)

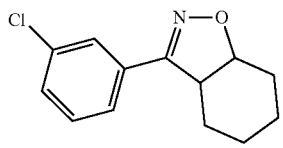 [SMILES: Clc1cccc(C2=NOC3CCCCC23)c1]

Yield 11%, a colorless wax; $^1$H NMR δ 7.68 (m, 1H), 7.59 (m, 1H), 7.37-7.31 (m, 2H), 4.51 (m, 1H), 3.23 (m, 1H), 2.27 (m, 1H), 1.97 (m, 1H), 1.77 (m, 1H), 1.71-1.60 (m, 2H), 1.54 (m, 1H), 1.27-1.22 (m, 2H); $^{13}$C NMR δ 163.3, 135.2 (2 s), 130.4, 130.3 (2 d), 128.3 (s), 127.3, 125.4, 81.1, 44.7 (4 d), 26.7, 25.4, 22.6, 20.5 (4 t).

3-(4-Chloro-phenyl)-3a,4,5,6,7,7a-hexahydro-benzo[d]-isoxazole (32)

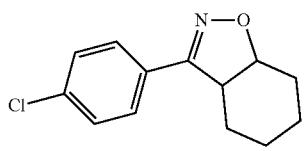 [SMILES: Clc1ccc(C2=NOC3CCCCC23)cc1]

Yield 25%, a colorless wax; $^1$H NMR δ 7.64 (m, 2H), 7.37 (m, 2H), 4.50 (m, 1H), 3.22 (m, 1H), 2.27 (m, 1H), 1.95 (m, 1H), 1.77 (m, 1H), 1.72-1.60 (m, 2H), 1.54 (m, 1H), 1.28-1.20 (m, 2H); $^{13}$C NMR δ 163.4, 136.3 (2 s), 129.5, 128.5 (2 d), 128.3 (s), 81.0, 44.7 (2 d), 26.8, 25.4, 22.7, 20.6 (4 t).

3-Naphthalen-1-yl-3a,4,5,6,7,7a-hexahydro-benzo[d]-isoxazole (33)

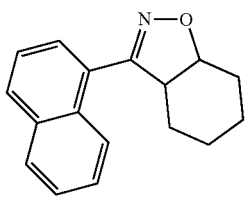 [SMILES: c1ccc2c(C3=NOC4CCCCC34)cccc2c1]

Yield 14%, a colorless wax; $^1$H NMR δ 8.78 (d, 1H, J=8.5), 7.86 (m, 2H), 7.57 (m, 2H), 7.52 (dd, 1H, J=7.0, 6.9), 7.48 (dd, 1H, J=7.9, 7.5), 4.65 (m, 1H), 3.53 (m, 1H), 2.20 (m, 1H), 1.84 (m, 1H), 1.61 (m, 1H), 1.60-1.52 (m, 2H), 1.40 (m, 1H), 1.30-1.20 (m, 2H); $^{13}$C NMR δ 164.5, 134.5, 131.7 (3 s), 130.8 (d), 130.2 (s), 128.9, 128.1, 127.7, 127.1, 126.7, 125.3, 79.8, 48.1 (8 d), 26.1, 26.0, 22.7, 20.7 (4 t); MS(EI) obs. 251.10.

3-(4-Nitro-phenyl)-3a,4,5,6,7,7a-hexahydro-benzo[d]-isoxazole (34)

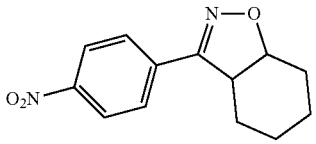 [SMILES: O=[N+]([O-])c1ccc(C2=NOC3CCCCC23)cc1]

Yield 6%, a yellow viscous oil; $^1$H NMR δ 8.25 (m, 2H), 7.88 (m, 2H), 4.58 (m, 1H), 3.30 (m, 1H), 2.30 (m, 1H), 2.00 (m, 1H), 1.81 (m, 1H), 1.75-1.64 (m, 2H), 1.55 (m, 1H), 1.33-1.21 (m, 2H). MS(EI) obs. 246.05. [Giurg, M.; Mlochowski, J.; *Polish J. Chem.* 1997, 71, 1093-1101].

3-(4-Fluoro-3-trifluoromethyl-phenyl)-3a,4,5,6,7,7a-hexahydro-benzo-[d]-isoxazole (35)

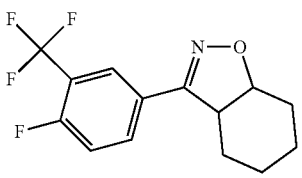 [SMILES: Fc1ccc(C2=NOC3CCCCC23)cc1C(F)(F)F]

Yield 55%, a yellow wax; $^1$H NMR δ 7.94-7.88 (m, 2H), 7.25 (dd, 1H, J=9.3, 9.2), 4.54 (m, 1H), 3.72 (m, 1H), 2.26 (m, 1H), 1.97 (m, 1H), 1.78 (m, 1H), 1.77-1.59 (m, 2H), 1.54 (m, 1H), 1.38-1.15 (m, 2H); $^{13}$C NMR δ 162.3 (s), 160.8, 138.7 (2 d), 132.6, 126.6 (2 dd), 126.1 (qd), 122.6 (q), 116.3 (dd), 81.4, 45.0 (2 d), 26.7, 25.3, 22.5, 20.4 (4 t).

3-(4-Fluoro-2-trifluoromethyl-phenyl)-3a,4,5,6,7,7a-hexahydro-benzo[d]-isoxazole (36)

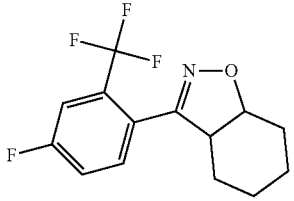 [SMILES: Fc1ccc(C2=NOC3CCCCC23)c(C(F)(F)F)c1]

Yield 51%, a yellow wax; $^1$H NMR δ 7.52 (m, 1H), 7.47 (m, 1H), 7.30 (m, 1H), 4.63 (m, 1H), 3.31 (m, 1H), 2.10 (m, 1H), 1.81 (m, 1H), 1.68 (m, 1H) 1.59-1.52 (m, 3H), 1.38-1.20 (m, 2H); $^{13}$C NMR δ 163.1 (dd), 162.7 (s), 133.8 (dd), 131.4 (qd), 125.3 (d), 123.4 (qd), 119.3 (dd), 115.0 (ddq), 80.8, 48.4 (2 d), 25.8, 25.4, 22.3, 20.5 (4 t).

3-(4-Nitro-3-trifluoromethyl-phenyl)-3a,4,5,6,7,7a-hexahydro-benzo-[d]-isoxazole (37)

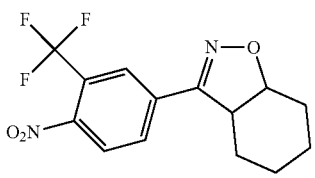 [SMILES: O=[N+]([O-])c1ccc(C2=NOC3CCCCC23)cc1C(F)(F)F]

Yield 1%, a yellow wax; $^1$H NMR δ 8.15 (d, 1H, J=1.7), 8.02 (dd, 1H, J=8.5, 1.7), 7.93 (d, 1H, J=8.5), 4.61 (m, 1H), 3.31 (m, 1H), 2.33 (m, 1H), 2.00 (m, 1H), 1.80 (m, 1H), 1.78-1.63 (m, 2H), 1.54 (m, 1H), 1.32-1.21 (m, 2H); MS(EI) obs. 314.10.

3-(4-Nitro-2-trifluoromethyl-phenyl)-3a,4,5,6,7,7a-hexahydro-benzo-[d]-isoxazole (38)

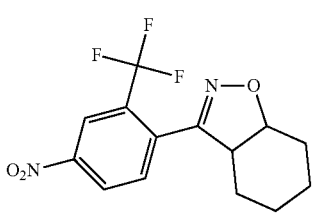 [SMILES: O=[N+]([O-])c1ccc(C2=NOC3CCCCC23)c(C(F)(F)F)c1]

Yield 4%, yellow viscous oil $^1$H NMR: δ 8.62 (d, 1H, J=2.1), 8.45 (dd, 1H, J=8.3, 2.1), 7.76 (d, 1H, J=8.3), 4.69 (m, 1H), 3.40 (m, 1H), 2.15 (m, 1H), 1.82 (m, 1H), 1.72-1.62 (m, 2H), 1.58 (m, 1H), 1.34-1.22 (m, 2H); MS(EI) obs. 314.10.

3-(4-Fluoro-3-trifluoromethyl-phenyl)-4,5,6,7,8,8a-hexahydro-3aH-cyclohepta[d]isoxazole (39)

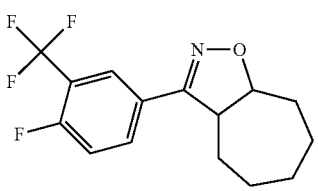 [SMILES: Fc1ccc(C2=NOC3CCCCCC23)cc1C(F)(F)F]

Yield 70%, a yellow wax; $^1$H NMR δ 7.90 (m, 1H), 7.83 (m, 1H), 7.24 (m, 1H), 4.91 (m, 1H), 3.72 (m, 1H), 2.05 (m, 1H, 1H), 1.98 (m, 1H), 1.83-1.47 (m, 6H), 1.45-1.36 (m, 2H); $^{13}$C NMR δ 160.7 (dd), 157.0 (s), 132.7 (dd), 126.6 (d), 126.2 (qd), 122.7 (q), 119.3 (qd), 117.9 (dd), 85.9, 51.5 (2 d), 31.4, 30.5, 28.4, 27.4, 24.1 (5 t).

3-(4-Fluoro-2-trifluoromethyl-phenyl)-4,5,6,7,8,8a-hexahydro-3aH-cyclohepta[d]isoxazole (40)

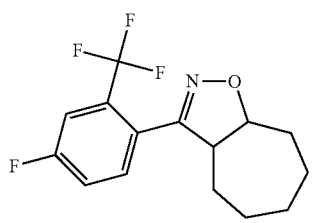 [SMILES: Fc1ccc(C2=NOC3CCCCCC23)c(C(F)(F)F)c1]

Yield 73%, a yellow wax; $^1$H NMR δ 7.49-7.43 (m, 2H), 7.29 (m, 1H), 4.92 (m, 1H), 3.71 (m, 1H), 2.07 (m, 1H), 1.94 (m, 1H), 1.85 (m, 1H) 1.73-1.62 (m, 2H), 1.59-1.45 (m, 3H), 1.38 (m, 1H), 1.27 (m, 1H); $^{13}$C NMR δ 163.0 (dd), 158.9 (s), 134.0 (dd), 131.5 (qd), 125.7 (d), 123.7 (qd), 119.4 (dd), 114.7 (ddq), 85.6, 55.0 (2 d), 31.6, 30.7, 28.6, 27.5, 24.6 (5 t).

3-(4-Nitro-3-trifluoromethyl-phenyl)-4,5,6,7,8,8a-hexahydro-3aH-cyclohepta[d]isoxazole (41)

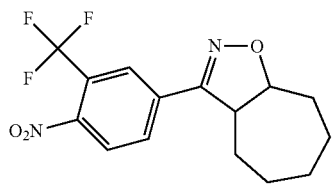 [SMILES: O=[N+]([O-])c1ccc(C2=NOC3CCCCCC23)cc1C(F)(F)F]

Yield 58%, a yellow wax; $^1$H NMR δ 8.14 (d, 1H, J=1.5), 7.95 (dd, 1H, J=8.5, 1.5), 7.94 (d, 1H, J=8.5), 4.99 (m, 1H), 3.77 (m, 1H), 2.09 (m, 1H), 2.01 (m, 1H), 1.81 (m, 1H) 1.79-1.60 (m, 2H), 1.60-1.52 (m, 3H), 1.51-1.42 (m, 2H); $^{13}$C NMR δ 157.9, 148.2, 134.8 (3 s), 131.2 (d), 126.6 (q), 126.2 (d), 124.5 (dq), 122.1 (q), 86.9, 50.9 (2 d), 31.3, 30.4, 28.3, 27.4, 24.0 (5 t).

3-(4-Nitro-2-trifluoromethyl-phenyl)-4,5,6,7,8,8a-hexahydro-3aH-cyclohepta[d]isoxazole (42)

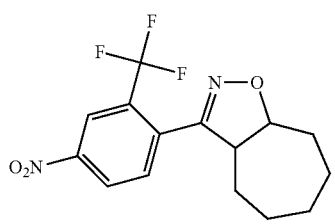 [SMILES: O=[N+]([O-])c1ccc(C2=NOC3CCCCCC23)c(C(F)(F)F)c1]

Yield 24%, yellow viscous oil $^1$H NMR: δ 8.62 (d, 1H, J=2.1), 8.44 (dd, 1H, J=8.3, 2.1), 7.72 (d, 1H, J=8.3), 4.99 (m, 1H), 3.80 (m, 1H), 2.81 (m, 1H), 2.08 (m, 1H), 1.95 (m, 1H), 1.87 (m, 1H), 1.34-1.22 (m, 2H).

3-(4-Fluoro-3-trifluoromethyl-phenyl)-3a,4,5,6,7,8,9,9a-octahydro-cycloocta[d]isoxazole (43)

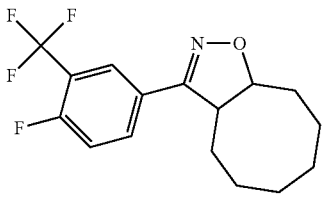 [SMILES: Fc1ccc(C2=NOC3CCCCCCC23)cc1C(F)(F)F]

Yield 63%, a yellow wax; $^1$H NMR δ 7.92 (d, 1H, J=7.0), 7.84 (m, 1H), 7.26 (m, 1H), 4.54 (m, 1H), 3.42 (m, 1H), 2.06 (m, 1H), 1.88-1.73 (m, 4H), 1.68 (m, 1H), 1.60-1.50 (m, 2H), 1.42-1.25 (m, 3H); $^{13}$C NMR δ 160.6 (dd), 160.8 (s), 132.7 (dd), 126.6 (d), 126.2 (qd), 122.6 (q), 119.3 (qd), 117.9 (dd), 86.6, 50.3 (2 d), 30.4, 25.8, 25.7, 25.6, 25.2, 24.8 (6 t).

3-(4-Fluoro-2-trifluoromethyl-phenyl)-3a,4,5,6,7,8,9,9a-octahydro-cycloocta[d]isoxazole (44)

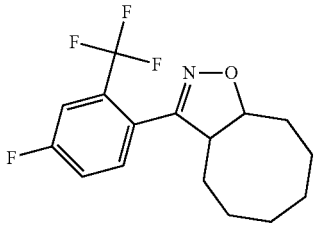 [SMILES: Fc1ccc(C2=NOC3CCCCCCC23)c(C(F)(F)F)c1]

Yield 30%, a yellow wax; $^1$H NMR δ 7.44 (dd, 1H, J=8.5, 5.5), 7.42 (dd, 1H, J=9.1, 2.7), 7.26 (m, 1H), 4.63 (m, 1H), 3.41 (m, 1H), 2.00-1.91 (m, 2H), 1.70-1.41 (m, 6H), 1.40-1.10 (m, 4H); $^{13}$C NMR δ 163.1 (dd), 160.5 (s), 134.4 (dd), 131.5 (qd), 125.4 (d), 123.3 (qd), 119.3 (dd), 115.0 (ddq), 86.1, 53.7 (2 d), 30.1, 26.7, 26.4, 25.7, 25.6, 24.2 (6 t).

3-(4-Nitro-3-trifluoromethyl-phenyl)-3a,4,5,6,7,8,9,9a-octahydro-cycloocta[d]isoxazole (45)

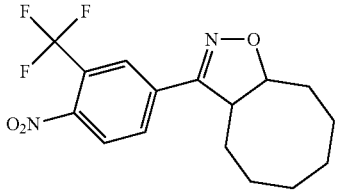 [SMILES: O=[N+]([O-])c1ccc(C2=NOC3CCCCCCC23)cc1C(F)(F)F]

Yield 17%, a yellow wax; $^1$H NMR δ 8.10 (s, 1H), 7.91-7.89 (m, 2H), 4.58 (m, 1H), 3.42 (m, 1H), 2.12 (m, 1H), 2.01 (m, 1H), 1.82-1.70 (m, 4H), 1.66 (m, 1H), 1.55-1.44 (m, 2H), 1.40-1.25 (m, 3H); $^{13}$C NMR δ 160.1, 148.3, 134.7 (3 s), 131.1 (d), 126.6 (q), 126.2 (d), 124.9 (dq), 122.1 (q), 87.6, 49.7 (2 d), 30.3, 25.8, 25.6, 25.6, 25.2, 24.9 (6 t).

3-(4-Nitro-2-trifluoromethyl-phenyl)-3a,4,5,6,7,8,9,9a-octahydro-cycloocta[d]isoxazole (46)

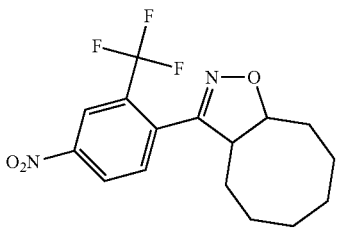 [SMILES: O=[N+]([O-])c1ccc(C2=NOC3CCCCCCC23)c(C(F)(F)F)c1]

Yield 16%, yellow viscous oil $^1$H NMR δ 8.60 (d, 1H, J=2.2), 8.42 (dd, 1H, J=8.4, 2.2), 7.70 (d, 1H, J=8.4), 4.70 (dd, 1H, J=10.4, 10.3), 3.51 (t, 1H, J=10.4), 2.08-1.94 (m, 2H), 1.75-1.43 (m, 6H), 1.43-1.20 (m, 3H), 1.13 (m, 1H).

3-Benzyl-3a,4,5,6,7,7a-hexahydro-benzo[d]isoxazole (47)

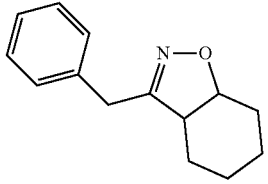 [SMILES: c1ccc(CC2=NOC3CCCCC23)cc1]

Yield 16%, a colorless wax; $^1$H NMR δ 7.31 (m, 2H), 7.28-7.24 (m, 3H), 4.34 (m, 1H), 3.82 (d, 1H, J=15.0), 3.53 (d, 1H, J=15.0), 2.73 (m, 1H), 1.94 (m, 1H), 1.73-1.61 (m, 2H), 1.51-1.40 (m, 3H), 1.29 (m, 1H), 1.18 (m, 1H); $^{13}$C NMR δ 164.6, 136.4 (2 s), 129.3, 129.2, 127.4, 79.7, 46.0 (5 d), 33.6, 26.0, 25.1, 22.5, 20.7 (4 t).

5-Benzyl-4-butyl-3-(4-methoxy-phenyl)-5-methyl-4,5-dihydro-[1,2,4]oxadiazole (48)

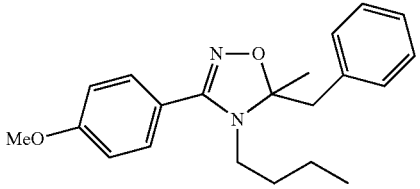 [SMILES: CCCCN1C(c2ccc(OC)cc2)=NOC1(C)Cc1ccccc1]

Yield 23%, pale brown viscous oil, $^1$H NMR δ 7.35 (m, 2H), 7.32-7.24 (m, 4H), 7.22 (m, 1H), 6.89 (m, 2H), 3.81 (s, 3H), 3.10 (m, 1H), 3.03 (d, 1H, J=13.7), 2.96 (d, 1H, J=13.7), 2.91 (m, 1H), 1.59 (s, 3H), 1.41 (m, 1H), 1.29 (m, 1H), 1.14 (m, 2H), 0.79 (t, 1H, J=7.3); $^{13}$C NMR δ 161.1, 157.4, 136.1 (3 s), 130.7, 129.7, 127.9, 126.6 (4 d), 118.5 (s), 114.1 (d), 100.1 (s), 55.3 (q), 45.8, 43.6, 33.0 (3 t), 22.6 (q), 20.0 (t), 13.6 (q).

5-Benzyl-4-butyl-3-(2-fluoro-phenyl)-5-methyl-4,5-dihydro-[1,2,4]oxadiazole (49)

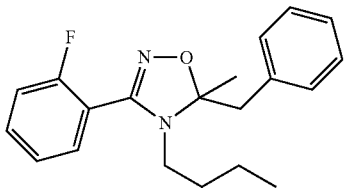 [SMILES: CCCCN1C(c2ccccc2F)=NOC1(C)Cc1ccccc1]

Yield 11%, brown viscous oil, $^1$H NMR δ 7.42 (m, 1H), 7.38 (m, 2H), 7.30 (m, 2H), 7.28-7.23 (m, 2H), 7.16 (t, 1H, J=7.5), 7.12 (t, 1H, J=9.1), 3.12 (d, 1H, J=13.8), 3.00 (m, 1H), 2.99 (d, 1H, J=13.8), 2.87 (ddd, 1H, J=15.4, 10.1, 5.8), 1.58 (s, 3H), 1.35 (m, 1H), 1.26 (m, 1H), 1.10 (m, 2H), 0.73 (t, 1H, J=7.3); $^{13}$C NMR δ 160.2 (d), 153.3, 135.8 (2 s), 132.4, 131.5 (2 dd), 130.7, 128.0, 126.6 (3 d), 124.4, 116.0 (2 dd), 114.4 (d), 100.9 (s), 44.7, 43.0, 32.8 (3 t), 23.0 (q), 19.9 (t), 13.5 (q).

5-Benzyl-4-butyl-3-(3-chloro-phenyl)-5-methyl-4,5-dihydro-[1,2,4]oxadiazole (50)

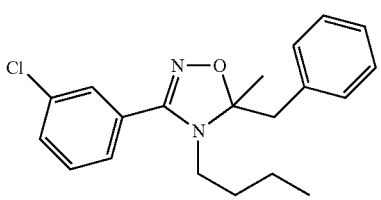 [SMILES: CCCCN1C(c2cccc(Cl)c2)=NOC1(C)Cc1ccccc1]

Yield 54%, pale brown viscous oil, $^1$H NMR δ 7.39 (d, 1H, J=7.5), 7.35 (m, 2H), 7.33-7.28 (m, 4H), 7.27-7.21 (m, 2H), 3.08 (m, 1H), 3.03 (d, 1H, J=13.8), 2.98 (d, 1H, J=13.8), 2.92 (m, 1H), 1.62 (s, 3H), 1.46 (m, 1H), 1.31 (m, 1H), 1.17 (m, 2H), 0.80 (t, 1H, J=7.4); $^{13}$C NMR δ 155.4, 135.7, 134.6 (3 s), 130.7, 130.4, 129.9, 128.4 (4 d), 128.1 (s), 128.0, 126.8, 126.4 (3 d), 100.9 (s), 45.9, 43.5, 33.0 (3 t), 22.9 (q), 19.9 (t), 13.6 (q).

5-Benzyl-4-butyl-5-methyl-3-(4-nitro-phenyl)-4,5-dihydro-[1,2,4]oxadiazole (51)

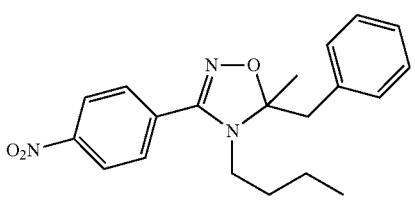 [SMILES: CCCCN1C(c2ccc([N+](=O)[O-])cc2)=NOC1(C)Cc1ccccc1]

Yield 29%, brown viscous oil, $^1$H NMR δ 8.23 (m, 2H), 7.50 (m, 2H), 7.35 (m, 2H), 7.30 (m, 2H), 7.25 (m, 1H), 3.10 (ddd, 1H, J=15.6, 10.5, 5.2), 3.02 (d, 1H, J=14.0), 3.01 (d, 1H, J=14.0), 2.95 (ddd, 1H, J=15.6, 10.9, 5.6), 1.66 (s, 3H), 1.46 (m, 1H), 1.29 (m, 1H), 1.17 (m, 2H), 0.81 (t, 1H, J=7.3); $^{13}$C NMR δ 155.8, 148.8, 135.6, 132.8 (4 s), 130.7, 129.1, 128.0, 126.8, 123.9 (5 d), 101.8 (s), 46.1, 43.7, 33.1 (3 t), 22.9 (q), 20.0 (t), 13.6 (q).

4-(5-Benzyl-4-butyl-5-methyl-4,5-dihydro-[1,2,4]oxadiazol-3-yl)-benzonitrile (52)

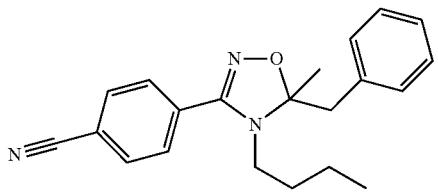 [SMILES: CCCCN1C(c2ccc(C#N)cc2)=NOC1(C)Cc1ccccc1]

Yield 23%, brown viscous oil, $^1$H NMR δ 7.67 (m, 2H), 7.44 (m, 2H), 7.34 (m, 2H), 7.29 (m, 2H), 7.23 (m, 1H), 3.09 (ddd, 1H, J=15.4, 10.6, 5.1), 3.01 (d, 1H, J=14.0), 3.00 (d, 1H, J=14.0), 2.92 (ddd, 1H, J=15.4, 10.9, 5.7), 1.64 (s, 3H), 1.43 (m, 1H), 1.27 (m, 1H), 1.16 (m, 2H), 0.80 (t, 1H, J=7.3); $^{13}$C NMR δ 156.1, 135.6 (2 s), 132.4 (d), 131.0 (s), 130.7, 128.8, 128.0, 126.8 (4 d), 118.1, 114.0, 101.5 (3 s), 46.1, 43.7, 33.0 (3 t), 22.9 (q), 19.9 (t), 13.6 (q).

5-Benzyl-4-butyl-5-methyl-3-napthalen-1-yl-4,5-dihydro-[1,2,4]oxadiazole (53)

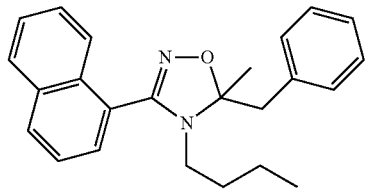 [SMILES: CCCCN1C(c2cccc3ccccc23)=NOC1(C)Cc1ccccc1]

Yield 14%, brown viscous oil, $^1$H NMR δ 7.87 (d, 1H, J=7.7), 7.80 (d, 1H, J=8.2), 7.49 (m, 2H), 7.47-7.41 (m, 2H), 7.39-7.32 (m, 6H), 3.19 (d, 1H, 14.2), 3.17 (d, 1H, 14.2), 2.84 (m, 2H), 1.68 (s, 3H), 1.26 (m, 1H), 1.15 (m, 1H), 0.92 (m, 2H), 0.54 (t, 3H, J=7.4); $^{13}$C NMR δ 155.9, 136.2, 133.3, 131.6 (4 s), 130.9, 130.4, 128.2, 128.2, 128.1 127.0, 126.8, 126.3, 125.1, 124.9 (10 d), 123.5, 101.0 (2 s), 45.0, 42.9, 32.8 (3 t), 24.9 (q), 19.8 (t), 13.3 (q).

5-Benzyl-4-butyl-5-methyl-3-napthalen-2-yl-4,5-dihydro-[1,2,4]oxadiazole (54)

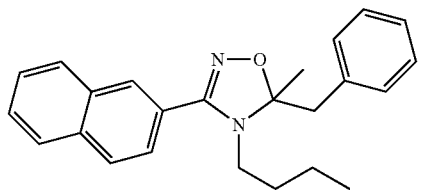 [SMILES: CCCCN1C(c2ccc3ccccc3c2)=NOC1(C)Cc1ccccc1]

Yield 26%, brown viscous oil, $^1$H NMR δ 7.87 (s, 1H), 7.85-7.81 (m, 3H), 7.51 (m, 2H), 7.44-7.39 (m, 3H), 7.31 (m, 2H), 7.25 (m, 1H), 3.16 (ddd, 1H, J=15.4, 10.5, 5.3), 3.09 (d, 1H, 13.8), 3.03 (d, 1H, 13.8), 2.85 (ddd, 1H, J=15.4, 10.7, 5.6), 1.64 (s, 3H), 1.46 (m, 1H), 1.34 (m, 1H), 1.13 (m, 2H), 0.76 (t, 3H, J=7.4); $^{13}$C NMR δ 157.7, 136.0, 134.0, 132.8 (4 s), 130.8, 128.4, 128.4, 128.4, 128.0, 127.8, 127.0, 126.6, 126.6 (10 d), 123.6, 100.6 (2 s), 45.8, 43.6, 33.0 (3 t), 22.8 (q), 19.9 (t), 13.6 (q).

3,5-Dibenzyl-4-butyl-5-methyl-4,5-dihydro-[1,2,4]oxadiazole (55)

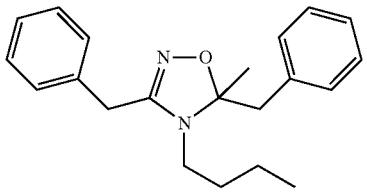 [SMILES: CCCCN1C(Cc2ccccc2)=NOC1(C)Cc1ccccc1]

Yield 34%, brown viscous oil, $^1$H NMR δ 7.27-7.20 (m, 8H), 7.08 (m, 2H), 3.61 (d, 1H, J=15.9), 3.43 (d, 1H, J=15.9), 2.96 (d, 1H, J=14.0), 2.86 (d, 1H, J=14.0), 2.86 (m, 1H), 2.74 (m, 1H), 1.44 (s, 3H), 1.48-1.22 (m, 2H), 1.14 (m, 2H), 0.81 (t, 1H, J=7.3); $^{13}$C NMR δ 155.0, 135.9, 134.6 (3 s), 130.6, 128.7, 128.3, 128.1, 127.0, 126.5 (6 d), 100.1 (s), 43.9, 42.1, 33.2, 30.2 (4 t), 23.6 (q), 20.1 (t), 13.7 (2 q).

5-Benzyl-4-butyl-3-(4-methoxy-benzyl)-5-methyl-4,5-dihydro-[1,2,4]oxadiazole (56)

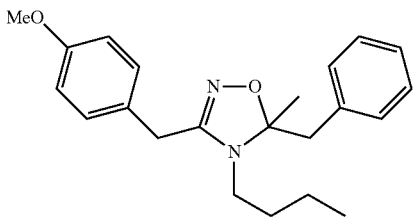 [SMILES: CCCCN1C(Cc2ccc(OC)cc2)=NOC1(C)Cc1ccccc1]

Yield 23%, brown viscous oil, $^1$H NMR δ 7.28-7.22 (m, 5H), 6.97 (m, 2H), 6.78 (m, 2H), 3.78 (s, 3H), 3.54 (d, 1H, J=15.9), 3.36 (d, 1H, J=15.9), 2.95 (d, 1H, J=14.0), 2.85 (d, 1H, J=14.0), 2.85 (m, 1H), 2.75 (m, 1H), 1.43 (s, 3H), 1.38-1.24 (m, 2H), 1.16 (m, 2H), 0.83 (t, 1H, J=7.3); $^{13}$C NMR δ 158.6, 155.2, 135.9 (3 s), 130.6, 129.4, 128.1 (3 d), 126.5 (s), 126.5, 114.2 (2 d), 100.0 (s), 55.3 (q), 43.9, 42.0, 33.3, 29.3 (4 t), 23.9 (q), 20.1 (t), 13.7 (q).

5-Benzyl-4-butyl-5-methyl-3-phenethyl-4,5-dihydro-[1,2,4]oxadiazole (57)

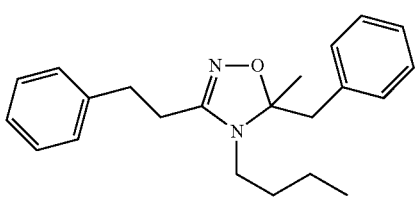 [SMILES: CCCCN1C(CCc2ccccc2)=NOC1(C)Cc1ccccc1]

Yield 31%, brown viscous oil, $^1$H NMR δ 7.31-7.27 (m, 4H), 7.27-7.25 (m, 2H), 7.21 (m, 1H), 7.19 (m, 1H), 7.15 (m, 2H), 3.04 (ddd, 1H, J=15.4, 9.9, 5.9), 2.95 (d, 1H, J=13.9), 2.94 (ddd, 1H, J=15.4, 10.0, 6.0), 2.83 (d, 1H, J=13.9), 2.74-2.67 (m, 2H), 2.42 (ddd, 1H, J=16.1, 10.5, 6.3), 2.28 (ddd, 1H, J=16.1, 10.7, 5.8), 1.47 (m, 2H), 1.46 (s, 3H), 1.29 (m, 2H), 0.92 (t, 3H, J=7.4); $^{13}$C NMR δ 156.0, 140.8, 135.9 (3 s), 130.6, 128.5, 128.3, 127.9, 126.5, 126.2 (6 d), 99.9 (s), 44.2, 42.1, 33.5, 32.0, 26.1 (5 t), 23.8 (q), 20.2 (t), 13.8 (q).

5-Benzyl-4-butyl-3-[2-(4-methoxy-phenyl)-ethyl]-5-methyl-4,5-dihydro-[1,2,4]oxadiazole (58)

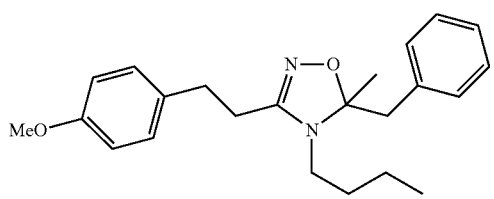 [SMILES: CCCCN1C(CCc2ccc(OC)cc2)=NOC1(C)Cc1ccccc1]

Yield 22%, brown viscous oil, $^1$H NMR δ 7.30-7.25 (m, 4H), 7.22 (m, 1H), 7.07 (m, 2H), 6.82 (m, 2H), 3.77 (s, 3H), 3.04 (ddd, 1H, J=15.4, 9.8, 6.0), 2.95 (d, 1H, J=13.9), 2.94 (ddd, 1H, J=15.4, 10.0, 5.9), 2.83 (d, 1H, J=13.9), 2.70-2.67 (m, 2H), 2.39 (ddd, 1H, J=15.5, 10.1, 6.5), 2.26 (ddd, 1H, J=15.5, 10.7, 5.8), 1.47 (m, 2H), 1.46 (s, 3H), 1.29 (m, 2H), 0.92 (t, 3H, J=7.3); $^{13}$C NMR δ 158.1, 156.0, 136.0, 132.9 (4 s), 130.6, 129.3, 129.2, 126.5, 114.0 (5 d), 99.9 (s), 55.3 (q), 44.2, 42.1, 33.6, 31.2, 26.4 (5 t), 23.7 (q), 20.2 (t), 13.7 (q).

5-Benzyl-4-butyl-5-methyl-3-(3-phenyl-propyl)-4,5-dihydro-[1,2,4]oxadiazole (59)

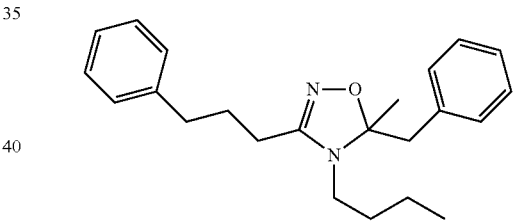

Yield 13%, brown viscous oil, $^1$H NMR δ 7.28 (m, 2H), 7.27-7.23 (m, 4H), 7.18 (m, 2H), 7.12 (m, 2H), 2.95 (m, 1H), 2.94 (d, 1H, J=13.9), 2.91 (m, 1H), 2.83 (d, 1H, J=13.9), 2.66-2.55 (m, 2H), 2.12 (m, 1H), 2.01 (m, 1H), 1.70 (m, 2H), 1.61 (m, 2H), 1.45 (s, 3H), 1.24 (m 2H), 0.89 (t, 3H, J=7.3); $^{13}$C NMR δ 156.2, 141.3, 135.9 (3 s), 130.6, 128.5, 128.3, 128.3, 126.5, 126.0 (6 d), 99.7 (s), 44.2, 42.1, 33.5, 32.3, 27.6, 27.2 (6 t), 23.8 (q), 20.1 (t), 13.7 (q).

5-Benzyl-3-(2-fluoro-phenyl)-4-isobutyl-5-methyl-4,5-dihydro-[1,2,4]oxadiazole (60)

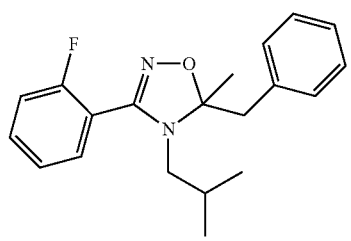 [SMILES: CC(C)CN1C(c2ccccc2F)=NOC1(C)Cc1ccccc1]

Yield 5%, pale brown viscous oil, $^1$H NMR δ 7.43 (m, 1H), 7.38 (m, 2H), 7.31 (m, 2H), 7.28-7.23 (m, 2H), 7.176 (m, 1H), 7.13 (m, 1H), 3.21 (d, 1H, J=13.7), 2.95 (d, 1H, J=13.7), 2.87 (dd, 1H, J=15.3, 7.7), 2.87 (dd, 1H, J=15.3, 7.6), 1.55 (s, 3H), 1.55 (m, 1H), 0.76 (d, 1H, J=6.6), 0.69 (d, 1H, J=6.6); $^{13}$C NMR δ 160.8 (d), 153.7, 135.8 (2 s), 132.4, 131.5 (2 dd), 130.8, 128.1, 126.6 (3 d), 124.4, 116.0 (2 dd), 114.5 (d), 101.2 (s), 50.6, 43.5 (2 t), 29.5 (d), 22.8, 20.1, 20.0 (3 q).

5-Benzyl-4-isobutyl-5-methyl-3-(4-nitro-phenyl)-4,5-dihydro-[1,2,4]oxadiazole (61)

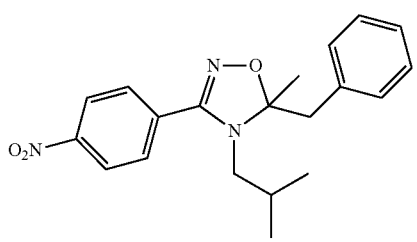 [SMILES: CC(C)CN1C(c2ccc([N+](=O)[O-])cc2)=NOC1(C)Cc1ccccc1]

Yield 29%, yellow wax, $^1$H NMR δ 8.21 (m, 2H), 7.44 (m, 2H), 7.38 (m, 2H), 7.31 (m, 2H), 7.25 (m, 1H), 3.10 (d, 1H, J=14.0), 2.98 (dd, 1H, J=14.9, 7.7), 2.98 (d, 1H, J=14.0), 2.79 (dd, 1H, J=14.9, 8.2), 1.65 (s, 3H), 1.63 (m, 1H), 0.87 (d, 1H, J=6.6), 0.73 (d, 1H, J=6.6); $^{13}$C NMR δ 156.0, 148.8, 135.5, 132.9 (4 s), 130.7, 129.6, 128.1, 126.9, 123.7 (5 d), 101.9 (s), 51.2, 45.5 (2 t), 28.6 (d), 23.3, 20.2, 20.1 (3 q).

4-(5-Benzyl-4-isobutyl-5-methyl-4,5-dihydro-[1,2,4]oxadiazol-3-yl)-benzonitrile (62)

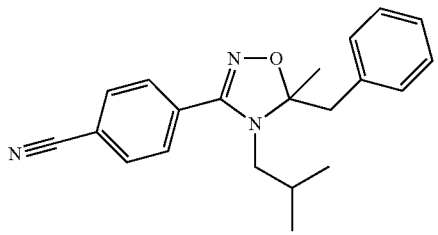 [SMILES: CC(C)CN1C(c2ccc(C#N)cc2)=NOC1(C)Cc1ccccc1]

Yield 5%, yellow wax, $^1$H NMR δ 7.67 (m, 2H), 7.66 (m, 2H), 7.38 (m, 2H), 7.30 (m, 2H), 7.25 (m, 1H), 3.09 (d, 1H, J=14.0), 2.97 d, 1H, J=14.0), 2.96 (dd, 1H, J=14.9, 7.0), 2.76 (dd, 1H, J=14.9, 8.2), 1.63 (s, 3H), 1.63 (m, 1H), 0.86 (d, 1H, J=6.6), 0.73 (d, 1H, J=6.6); $^{13}$C NMR δ 157.1, 135.9 (2 s), 132.9 (d), 131.4 (s), 131.1, 129.7, 128.5, 127.8 (4 d), 118.4, 113.6, 102.2 (3 s), 51.2, 45.5 (2 t), 29.0 (d), 23.7, 20.6, 20.5 (3 q).

5-Benzyl-4-isobutyl-5-methyl-3-napthalen-1-yl-4,5-dihydro-[1,2,4]oxadiazole (63)

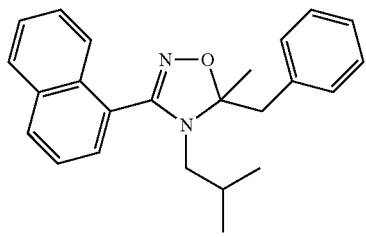 [SMILES: CC(C)CN1C(c2cccc3ccccc23)=NOC1(C)Cc1ccccc1]

Yield 8%, brown viscous oil, $^1$H NMR δ 7.88 (d, 1H, J=8.3), 7.81 (d, 1H, J=8.1), 7.51 (m, 2H), 7.48-7.30 (m, 8H), 3.28 (d, 1H, 14.1), 3.10 (d, 1H, 14.1), 2.74 (m, 2H), 1.66 (s, 3H), 1.38 (m, 1H), 0.64 (d, 3H, J=6.7), 0.54 (d, 3H, J=6.7); $^{13}$C NMR δ 156.2, 136.0, 133.3, 131.8 (4 s), 131.0, 130.4, 128.3, 128.3, 128.1, 127.0, 126.8, 126.3, 125.2, 124.8 (10 d), 123.5, 101.1 (2 s), 50.6, 44.3 (2 t), 27.9 (d), 24.5, 20.1, 20.0 (3 q).

5-Benzyl-4-isobutyl-5-methyl-3-napthalen-2-yl-4,5-dihydro-[1,2,4]oxadiazole (64)

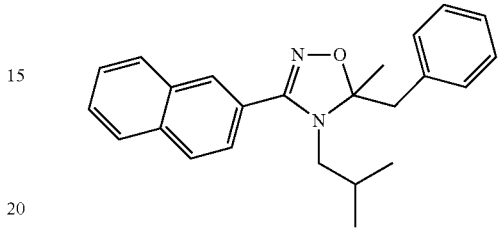

Yield 25%, pale brown viscous oil, $^1$H NMR δ 7.86-7.81 (m, 3H), 7.83 (s, 1H), 7.51 (m, 1H), 7.50 (m, 1H), 7.43 (m, 2H), 7.38 (m, 1H), 7.33 (m, 2H), 7.26 (m, 1H), 3.18 (d, 1H, 13.8), 3.06 (dd, 1H, J=14.8, 7.0), 3.2.99 (d, 1H, 13.8), 2.85 (dd, 1H, J=14.8, 8.2), 1.65 (m, 1H), 1.63 (s, 3H), 0.86 (d, 1H, J=6.6), 0.72 (d, 1H, J=6.6); $^{13}$C NMR δ 157.9, 136.0, 133.9, 132.8 (4 s), 130.8, 128.9, 128.4, 128.3, 128.1, 127.8, 127.2, 126.7, 126.6, 125.3 (10 d), 123.7, 100.9 (2 s), 51.2, 45.2 (2 t), 28.5 (d), 23.0, 20.2, 20.1 (3 q).

5-Benzyl-4-isobutyl-3-(4-methoxy-benzyl)-5-methyl-4,5-dihydro-[1,2,4]oxadiazole (65)

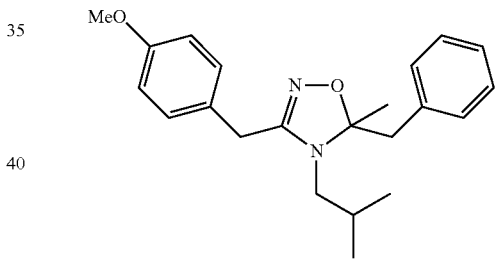

Yield 25%, brown viscous oil, $^1$H NMR δ 7.28-7.22 (m, 5H), 7.03 (m, 2H), 6.80 (m, 2H), 3.77 (s, 3H), 3.60 (d, 1H, J=15.9), 3.40 (d, 1H, J=15.9), 3.01 (d, 1H, J=13.8), 2.75 (d, 1H, J=13.8), 2.68 (dd, 1H, J=14.8, 7.7), 2.57 (dd, 1H, J=14.8, 7.8), 1.78 (m, 1H), 1.40 (s, 3H), 0.82 (d, 1H, J=6.7), 0.80 (d, 1H, J=6.7); $^{13}$C NMR δ 158.6, 155.9, 135.9 (3 s), 130.7, 129.5, 128.1, 126.5 (4 d), 126.3 (s), 114.2 (d), 100.0 (s), 55.2 (q), 49.9, 43.0, 29.5 (3 t), 28.7 (d), 23.2, 20.1, 20.1.7 (3 q).

5-Benzyl-4-isobutyl-5-methyl-3-phenethyl-4,5-dihydro-[1,2,4]oxadiazole (66)

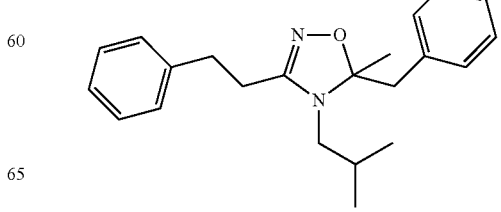

Yield 6%, pale brown viscous oil, $^1$H NMR δ 7.31-7.27 (m, 4H), 7.27-7.25 (m, 2H), 7.21 (m, 1H), 7.19 (m, 1H), 7.16 (m, 2H), 3.00 (d, 1H, J=13.8), 3.04 (dd, 1H, J=14.9, 7.8), 2.82-2.69 (m, 4H), 2.44 (ddd, 1H, J=16.6, 11.0, 5.6), 2.29 (ddd, 1H, J=16.6, 11.1, 5.3), 1.82 (m, 1H), 1.45 (s, 3H), 0.91 (d, 1H, J=6.7), 0.91 (d, 1H, J=6.7); $^{13}$C NMR δ 156.8, 140.9, 135.9 (3 s), 130.7, 128.6, 128.3, 128.0, 126.5, 126.3 (6 d), 100.2 (s), 50.1, 43.4, 31.7 (3 t), 29.0 (d), 26.4 (t), 23.5, 20.3, 20.2 (3 q).

5-Benzyl-4-isobutyl-3-[2-(4-methoxy-phenyl)-ethyl]-5-methyl-4,5-dihydro-[1,2,4]oxadiazole (67)

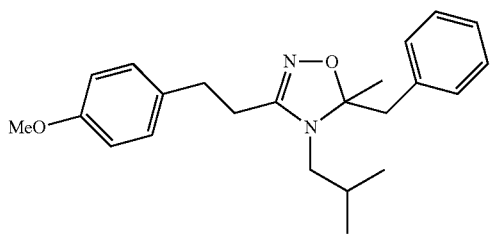 [SMILES: COc1ccc(CCC2=NOC(C)(Cc3ccccc3)N2CC(C)C)cc1]

Yield 23%, brown viscous oil, $^1$H NMR δ 7.32-7.24 (m, 4H), 7.22 (m, 1H), 7.08 (m, 2H), 6.83 (m, 2H), 3.77 (s, 3H), 3.00 (d, 1H, J=13.8), 2.83 (dd, 1H, J=14.9, 7.8), 2.79 (dd, 1H, J=14.9, 7.7), 2.78 (d, 1H, J=13.8), 2.67 (m, 2H), 2.40 (ddd, 1H, J=15.7, 10.8, 5.9), 2.26 (ddd, 1H, J=15.7, 11.1, 5.5), 1.82 (m, 1H), 1.44 (s, 3H), 0.92 (d, 3H, J=6.5), 0.91 (d, 3H, J=6.5); $^{13}$C NMR δ 158.1, 156.8, 135.9, 133.0 (4 s), 130.7, 129.3, 128.0, 126.5, 114.0 (5 d), 100.1 (s), 55.3 (q), 50.1, 43.4, 30.9 (3 t), 29.0 (d), 26.7 (t), 23.4, 20.3, 20.2 (3 q).

5-Benzyl-4-isobutyl-5-methyl-3-(3-phenyl-propyl)-4,5-dihydro-[1,2,4]oxadiazole (68)

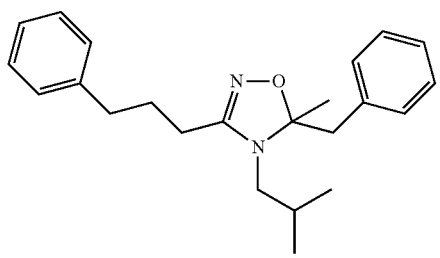 [SMILES: CC(C)CN1C(CCCc2ccccc2)=NOC1(C)Cc1ccccc1]

Yield 13%, pale brown viscous oil, $^1$H NMR δ 7.32-7.24 (m, 6H), 7.21-7.17 (m, 2H), 7.13 (m, 2H), 2.99 (d, 1H, J=13.8), 2.82-2.72 (m, 3H), 2.66-2.57 (m, 2H), 2.14 (m, 1H), 2.02 (m, 1H), 1.76 (m, 3H), 1.42 (s, 3H), 0.86 (d, 3H, J=6.7), 0.84 (d, 3H, J=6.7); $^{13}$C NMR δ 156.0, 141.3, 135.9 (3 s), 130.6, 128.5, 128.3, 128.0, 126.5, 126.0 (6 d), 99.9 (s), 50.0, 43.3, 35.1 (3 t), 29.0 (d), 27.1 (t), 23.5 (q), 23.2 (t), 20.2, 20.1 (2 q).

Methyl 3-(3-chloro-phenyl)-4,5,6,6a-tetrahydro-3aH-cyclopenta[d]isoxazole-5-carboxylate (69)

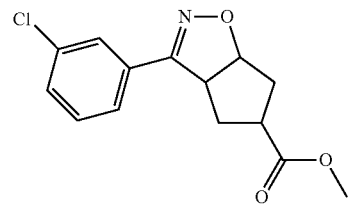 [SMILES: COC(=O)C1CC2ON=C(c3cccc(Cl)c3)C2C1]

Yield 89%, colourless viscous oil, $^1$H NMR δ 7.65 (m, 1H), 7.55 (d, 1H, J=7.5), 7.39 (d, 1H, J=8.5), 7.32 (dd, 1H, J=7.9, 7.7), 5.28 (dd, 1H, J=8.7, 5.2), 4.11 (m, 1H), 3.68 (s, 3H), 2.85 (m, 1H), 2.46 (dd, 1H, J=14.2, 6.3), 2.22-2.17 (m, 2H), 2.14 (ddd, 1H, 14.2, 11.9, 5.2); $^{13}$C NMR δ 174.4, 157.2, 134.9, 130.7 (4 s), 130.1, 130.0, 126.9, 125.0, 87.1 (5 d), 52.0 (q), 51.3, 41.6 (2 d), 39.1, 34.9 (2 t).

3-(3-Chloro-phenyl)-4,5,6,6a-tetrahydro-3aH-cyclopenta[d]isoxazole-5-carboxylic acid (70)

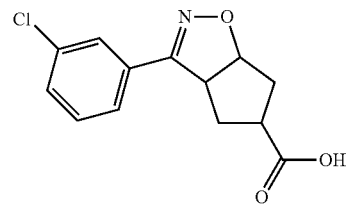 [SMILES: O=C(O)C1CC2ON=C(c3cccc(Cl)c3)C2C1]

Yield 38%, colourless viscous oil, $^1$H NMR δ 7.65 (m, 1H), 7.55 (d, 1H, J=7.6), 7.38 (d, 1H, J=8.5), 7.33 (dd, 1H, J=7.8, 7.6), 5.29 (dd, 1H, J=8.7, 5.1), 4.13 (m, 1H), 2.88 (m, 1H), 2.49 (dd, 1H, J=13.9, 5.9), 2.25-2.29 (m, 2H), 2.14 (m, 1H); $^{13}$C NMR δ 179.1, 157.2, 134.9, 130.5 (4 s), 130.1, 130.0, 126.9, 125.0, 87.1 (5 d), 51.3, 41.5 (2 d), 39.0, 34.7 (2 t).

3-(4-Fluoro-3-trifluoromethyl-phenyl)-4,5,6,6a-tetrahydro-3aH-cyclopenta[d]isoxazol-5-ylmethyl acetate (71)

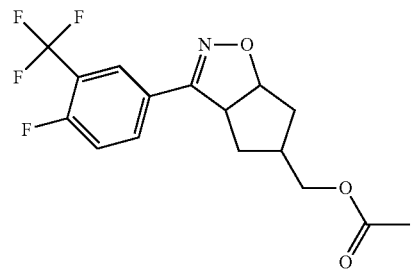 [SMILES: CC(=O)OCC1CC2ON=C(c3ccc(F)c(C(F)(F)F)c3)C2C1]

Yield 90%, colourless viscous oil, $^1$H NMR δ 7.89 (d, 1H, J=6.7), 7.87 (m, 1H), 7.25 (m, 1H), 5.28 (dd, 1H, J=8.8, 5.6), 4.11-4.05 (m, 3H), 2.33 (m, 2H), 2.04 (s, 3H), 1.99 (m, 1H), 1.75 (m, 1H), 1.66 (m, 1H); $^{13}$C NMR δ 170.9 (s), 160.3 (dd), 156.5 (s), 132.2 (dd), 125.8 (d), 125.7 (qd), 122.2 (q), 119.1 (qd), 117.6 (dd), 87.8 (d), 66.0 (t), 51.3, 38.8 (2 d), 36.7, 34.4 (2 t), 20.8 (q).

[3-(4-Fluoro-3-trifluoromethyl-phenyl)-4,5,6,6a-tetrahydro-3aH-cyclopenta[d]isoxazol-5-yl]-methanol (72)

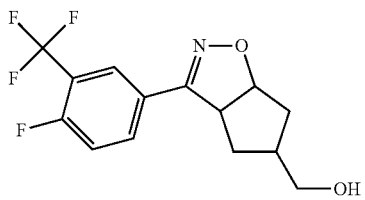 [SMILES: OCC1CC2ON=C(c3ccc(F)c(C(F)(F)F)c3)C2C1]

Yield 25%, colourless viscous oil; $^1$H NMR δ 7.90 (d, 1H, J=7.3), 7.87 (m, 1H), 7.24 (d, 1H, J=9.3), 5.28 (dd, 1H, J=8.9, 5.6), 4.08 (dd, 1H, J=9.2, 8.7), 3.70 (m, 1H), 3.62 (m, 1H), 2.30 (m, 1H), 2.22 (m, 1H), 2.02, (dd, 1H, J=13.1, 6.2), 1.78 (ddd, 1H, J=20.9, 11.6, 9.4), 1.67 (ddd, 1H, J=13.3, 8.05, 1.9), 1.34 (br s, 1H, OH); $^{13}$C NMR δ 160.3 (dd), 156.6 (s), 132.2 (dd), 125.7 (d), 125.6 (qd), 122.2 (q), 119.1 (qd), 117.5 (dd), 88.0 (d), 64.9 (t), 51.4, 39.9 (2 d), 38.4, 34.2 (2 t).

2-[3-(4-Fluoro-3-trifluoromethyl-phenyl)-4,5,6,6a-tetrahydro-3aH-cyclopenta[d]isoxazol-6-yl]-ethyl acetate (73)

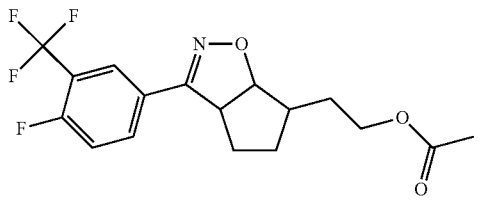 [SMILES: CC(=O)OCCC1CCC2C(c3ccc(F)c(C(F)(F)F)c3)=NOC12]

Yield 66%, colourless viscous oil, $^1$H NMR δ 7.91 (d, 1H, J=6.8), 7.87 (m, 1H), 7.24 (m, 1H), 5.12 (dd, 1H, J=8.6, 4.4), 4.19 (m, 2H), 4.05 (dd, 1H, J=8.6, 8.5), 2.07 (m, 2H), 2.07 (s, 3H), 2.02-1.82 (m, 4H), 1.27 (m, 1H); $^{13}$C NMR δ 171.1 (s), 160.3 (dd), 156.9 (s), 132.2 (dd), 125.8 (d), 125.7 (qd), 122.3 (q), 119.2 (qd), 117.6 (dd), 88.8 (d), 63.4 (t), 51.5, 45.1 (2 d), 30.2, 28.9, 27.9 (3 t), 21.0 (q).

2-[3-(4-Fluoro-3-trifluoromethyl-phenyl)-4,5,6,6a-tetrahydro-3aH-cyclopenta[d]isoxazol-4-yl]-ethyl acetate (74)

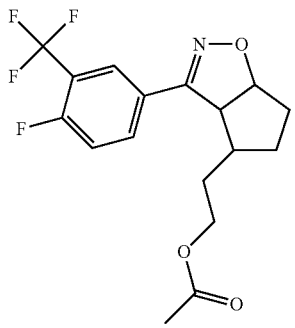 [SMILES: CC(=O)OCCC1CCC2ON=C(c3ccc(F)c(C(F)(F)F)c3)C12]

Yield 26%, colourless viscous oil, $^1$H NMR δ 7.90 (d, 1H, J=6.9), 7.88 (m, 1H), 7.24 (m, 1H), 5.16 (dd, 1H, J=8.6, 4.7), 4.04 (dd, 1H, J=8.6, 8.5), 3.80 (m, 1H), 2.21 (m, 1H), 1.99 (m, 1H), 1.97-1.80 (m, 4H), 1.35-1.22 (m, 2H).

3-(4-Chloro-phenyl)-4,5,6,7,8,8a-hexahydro-3aH-cyclohepta[d]isoxazol-8-yl acetate (75)

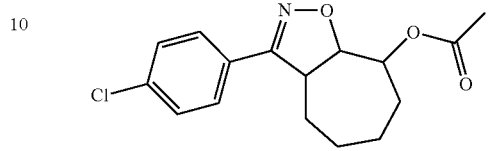

Yield 4%, colourless viscous oil, $^1$H NMR δ 7.58 (m, 2H), 7.37 (m, 2H), 5.21 (dd, 1H, J=10.3, 10.0), 4.81 (ddd, 1H, J=10.0, 8.8, 0.5), 3.90 (ddd, 1H, J=11.3, 10.3, 2.3), 2.11 (s, 3H), 1.92 (m, 1H), 1.89-1.77 (m, 3H), 1.76-1.55 (m, 3H), 1.32 (m, 1H); $^{13}$C NMR δ 170.2, 159.3, 136.0 (3 s), 129.2, 128.3 (2 d), 127.1 (s), 86.7, 75.3, 50.2 (3 d), 32.2, 28.5, 26.9, 26.7 (4 t), 21.3 (q).

3-(4-Chloro-phenyl)-4,5,6,7,8,8a-hexahydro-3aH-cyclohepta[d]isoxazol-4-yl acetate (76)

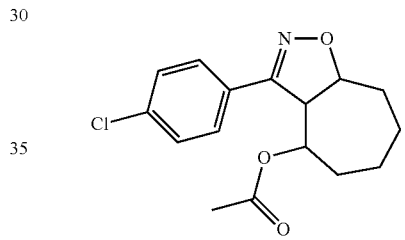

Yield 3%, colourless viscous oil, $^1$H NMR δ 7.54 (m, 2H), 7.36 (m, 2H), 5.17 (ddd, 1H, J=7.1, 3.0, 0.5), 4.92 (ddd, 1H, J=11.4, 9.3, 5.1), 3.90 (dd, 1H, J=11.4, 3.0), 2.23-2.10 (m, 2H), 2.03 (m, 1H), 1.90 (s, 3H), 1.84 (m, 1H), 1.63 (m, 2H), 1.53 (m, 1H), 1.42 (m, 1H); $^{13}$C NMR δ 169.8, 156.9, 135.8 (3 s), 129.0, 128.3 (2 d), 128.2 (s), 83.8, 71.7, 54.3 (3 d), 32.2, 30.1, 25.5, 23.3 (4 t), 20.9 (q).

3-(4-Chloro-phenyl)-4,5,6,7,8,8a-hexahydro-3aH-cyclohepta[d]isoxazol-8-ol (77)

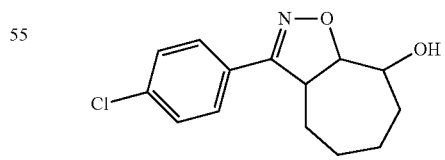

Yield 10%, colourless viscous oil, $^1$H NMR δ 7.56 (m, 2H), 7.38 (m, 2H), 4.65 (dd, 1H, J=10.6, 8.8), 4.06 (m, 1H), 3.68 (m, 1H), 2.31 (br s, 1H, OH), 1.98 (m, 1H), 1.92-1.83 (m, 1H), 1.66 (m, 1H), 1.49-1.40 (m, 2H), 1.27 (m, 1H); $^{13}$C NMR δ 159.6, 136.0 (2 s), 129.1, 128.4 (2 d), 127.2 (s), 90.0, 73.2, 50.0 (3 d), 34.0, 29.7, 28.7, 27.2 (4 t).

Examples 78-84

5-Benzyl-3-(2-hydroxy-phenyl)-5-phenyl-4,5-dihydro-isoxazole (78)

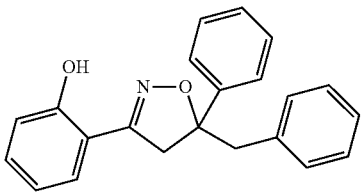 [SMILES: Oc1ccccc1C1=NOC(Cc2ccccc2)(c2ccccc2)C1]

Method B:

To a solution of 5-Benzyl-3-(2-methoxyphenyl)-5-phenyl-4,5-dihydroisoxazole (compound 12, 0.463 g, 2 mmol, synthesized using the general method described in Example 1) in 2 ml of dichloromethane was added 2.2 ml of 1M BBr$_3$ in dichloromethane (2.2 mmol; for compounds having two or three aromatic methoxyl groups, 4.2 mmol and 6.2 mmol was used, respectively) and the solution was stirred under argon at room temperature overnight. The organic layer was evaporated to give the oily product, which was purified by column chromatography using dichloromethane as an eluent.

Yield 83%, mp=107.5-108.9° C., $^1$H NMR δ 8.30 (br s, 1H, OH), 7.36 (m, 2H), 7.31 (m, 2H), 7.28-7.22 (m, 3H), 7.21-7.14 (m, 3H), 7.10-7.04 (m, 3H), 6.98 (d, 1H, J=7.4), 6.84 (dd, 1H, J=7.3, 7.2), 3.63 (d, 1H, J=16.4), 3.56 (d, 1H, J=16.4), 3.33 (d, 1H, J=14.0), 3.27 (d, 1H, J=14.0); $^{13}$C NMR δ 158.7, 157.3, 143.6, 135.4 (4 s), 131.6, 130.6, 128.4, 128.2, 128.1, 127.6, 126.9, 125.3, 119.3, 116.9 (10 d), 114.0 (s), 90.0 (s), 47.0, 45.5 (2 t).

The following compounds included in the invention were prepared by Method B using appropriate starting materials:

5-Benzyl-3-(3-hydroxyphenyl)-5-phenyl-4,5-dihydro-isoxazole (79)

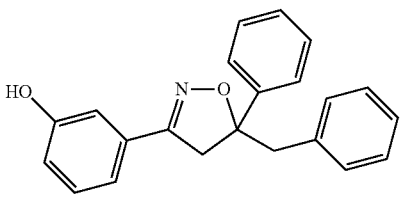 [SMILES: Oc1cccc(C2=NOC(Cc3ccccc3)(c3ccccc3)C2)c1]

Yield 45%, colorless viscous oil ° C., $^1$H NMR δ 7.34 (m, 2H), 7.30 (m, 2H), 7.24 (m, 1H), 7.18-7.13 (m, 5H), 7.06-7.03 (m, 3H), 6.88 (dd, 1H, J=8.2, 1.9), 6.65 (br s, 1H, OH), 3.53 (d, 1H, J=16.5), 3.43 (d, 1H, J=16.5), 3.28 (d, 1H, J=14.0), 3.23 (d, 1H, J=14.0); $^{13}$C NMR δ 156.9, 156.1, 144.1, 135.7 (4 s), 130.6 (d), 130.6 (s), 129.9, 128.3, 128.0, 127.4, 126.8, 125.3, 119.0, 117.0, 113.3 (9 d), 91.0 (s), 47.3, 45.5 (2 t).

5-Benzyl-3-(4-hydroxyphenyl)-5-phenyl-4,5-dihydro-isoxazole (80)

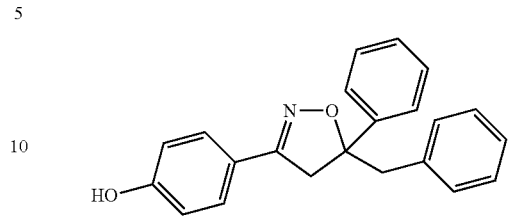

Yield 48%, mp=151.3-153.9° C., $^1$H NMR δ 7.42 (m, 2H), 7.36 (m, 2H), 7.31 (m, 2H), 7.25 (m, 1H), 7.19-7.15 (m, 3H), 7.07 (m, 2H), 6.79 (m, 2H), 6.34 (br s, 1H, OH), 3.55 (d, 1H, J=16.4), 3.44 (d, 1H, J=16.4), 3.29 (d, 1H, J=14.0), 3.24 (d, 1H, J=14.0); $^{13}$C NMR δ 158.8, 156.8, 144.4, 135.9 (4 s), 130.7, 128.3, 128.3, 128.0, 127.4, 126.7, 125.4 (7 d), 121.0 (s), 115.6 (d), 90.5 (s), 47.3, 45.8 (2 t).

3-[2-(2-Hydroxy-phenyl)-ethyl]-5-methyl-5-phenyl-4,5-dihydro-isoxazole (81)

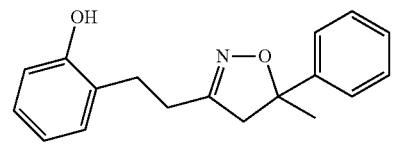 [SMILES: CC1(c2ccccc2)CC(CCc2ccccc2O)=NO1]

Yield 22%, brown viscous oil, $^1$H NMR δ 7.39-7.32 (m, 4H), 7.26 (m, 1H), 7.09 (m, 1H), 6.70 (m, 2H), 6.60 (m, 1H), 5.56 (br s, 1H, OH), 3.03 (d, 1H, J=16.9), 2.99 (d, 1H, J=16.9), 2.81 (t, 2H, J=7.5), 2.62 (t, 2H, J=7.5), 1.66 (s, 3H); $^{13}$C NMR δ 158.5, 156.0, 145.6, 142.0 (4 s), 129.7, 128.5, 127.3, 124.7, 120.5, 115.3, 113.5 (7d), 87.0 (s), 51.0, 32.5, 29.4 (3 t), 28.0 (q). [WO2009066009, compound 85]

3-[2-(3-Hydroxy-phenyl)-ethyl]-5-methyl-5-phenyl-4,5-dihydro-isoxazole (82)

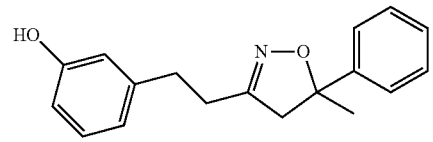 [SMILES: CC1(c2ccccc2)CC(CCc2cccc(O)c2)=NO1]

Yield 97%, brown viscous oil, $^1$H NMR δ 7.37-7.31 (m, 4H), 7.25 (t, 1H, J=6.9), 7.04 (t, 1H, J=7.6), 7.00 (d, 1H, J=7.5), 6.81 (d, 1H, J=7.9), 6.75 (t, 1H, J=7.4), 4.68 (br s, 1H, OH), 3.08 (d, 1H, J=17.1), 3.06 (d, 1H, J=17.1), 2.86 (t, 2H, J=7.5), 2.65 (t, 2H, J=7.3), 1.64 (s, 3H); $^{13}$C NMR δ 159.8, 154.9, 145.6, (3 s), 130.2, 128.5, 127.7, 127.4 (4 d), 127.0 (s), 124.7, 120.0, 115.7 (3 d), 87.1 (s), 51.0 (t), 28.3 (q), 28.0, 27.4 (2 t). [WO2009066009, compound 86]

3-[2-(4-Hydroxy-phenyl)-ethyl]-5-methyl-5-phenyl-4,5-dihydro-isoxazole (83)

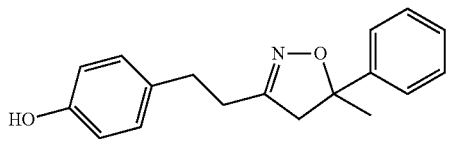 [SMILES: CC1(c2ccccc2)CC(CCc2ccc(O)cc2)=NO1]

Yield 19%, brown viscous oil, $^1$H NMR δ 7.38-7-32 (m, 4H), 7.26 (m, 1H), 6.96 (m, 2H), 6.69 (m, 2H), 3.03 (d, 1H, J=16.8), 2.99 (d, 1H, J=16.8), 2.79 (t, 2H, J=7.6), 2.61 (t, 2H, J=7.6), 1.65 (s, 3H); $^{13}$C NMR δ 158.4, 154.3, 145.6, 132.1 (4 s), 129.4, 128.5, 127.2, 124.7, 115.4 (5 d), 86.9 (s), 50.9, 31.8, 29.8 (3 t), 28.0 (q). [WO2009066009, compound 87]

3-[3-(4-Hydroxy-phenyl)-propyl]-5-methyl-5-phenyl-4,5-dihydro-isoxazole (84)

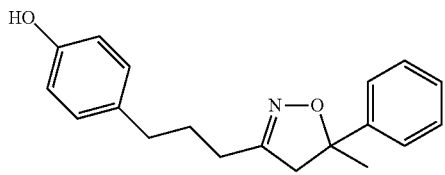 [SMILES: CC1(c2ccccc2)CC(CCCc2ccc(O)cc2)=NO1]

Yield 99%, a brown viscous oil, $^1$H NMR δ 7.40 (m, 2H), 7.33 (m, 2H), 7.24 (m, 2H), 6.92 (m, 2H), 6.75 (m, 2H), 6.54 (br s, 1H, OH), 3.06 (d, 1H, J=16.9), 3.02 (d, 1H, J=16.9), 2.49 (m, 2H), 2.31 (t, 2H, J=7.6), 1.79 (m, 2H), 1.69 (s, 3H); $^{13}$C NMR δ 159.3, 154.3, 145.5, 132.9 (4 s), 129.4, 128.5, 127.3, 124.6, 115.4 (5 d), 86.7 (s), 50.7, 34.2, 28.1 (3 t), 28.0 (q), 27.3 (t). [WO2009066009, compound 90]

Examples 85-95

4-(4,5,6,6a-Tetrahydro-3aH-cyclopenta[d]isoxazol-3-yl)-2-trifluoromethyl-benzonitrile (85)

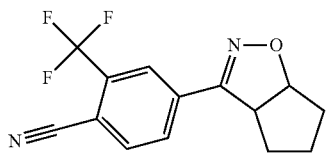 [SMILES: N#Cc1ccc(C2=NOC3CCCC23)cc1C(F)(F)F]

Method C:
In an oven-dried flask equipped with a condenser and stirrer, 3-(4-fluoro-3-trifluoromethyl-phenyl)-4,5,6,6a-tetrahydro-3aH-cyclopenta[d]-isoxazole (compound 18, 0.287 g, 1 mmol, synthesized using the general method described in Example 1) and potassium cyanide (0.160 g, 4 mmol) were dissolved in 10 ml of anhydrous dimethyl sulfoxide. The solution was stirred at 150-160° C. in argon atmosphere for 16 h, poured into 10 ml of 2M HCl, and extracted three times with 10 ml of dichloromethane. The organic extracts were combined and washed once with 10 ml of H$_2$O, dried with MgSO$_4$, evaporated to dryness, and purified by preparative TLC using dichloromethane as eluent (rf 0.8).

Yield 93%, a white wax; $^1$H NMR δ 8.14 (s, 1H), 7.95 (d, 1H, J=8.5), 7.87 (d, 1H, J=8.5), 5.35 (dd, 1H, J=9.0, 4.5), 4.03 (td, 1H, J=9.0, 2.0), 2.23 (m, 1H), 2.00-1.78 (m, 4H), 1.52 (m, 1H); $^{13}$C NMR δ 156.9 (s), 135.5, 134.9 (2 d), 133.7 (q), 130.2 (d), 125.1, 122.6 (2 q), 115.6 (d), 110.6 (s), 90.0, 51.3 (2 d), 36.0, 31.8, 23.9 (3 t).

4-(4,5,6,6a-Tetrahydro-3aH-cyclopenta[d]isoxazol-3-yl)-3-trifluoromethyl-benzonitrile (86)

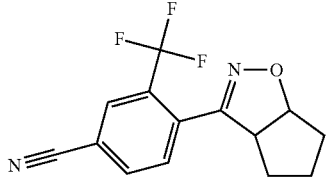 [SMILES: N#Cc1ccc(C2=NOC3CCCC23)c(C(F)(F)F)c1]

Yield 37%, a yellow wax; $^1$H NMR δ 8.00 (s, 1H), 7.85 (d, 1H, J=8.0), 7.60 (d, 1H, J=8.0), 5.27 (m, 1H), 4.08 (m, 1H), 2.15 (m, 1H), 1.77-1.69 (m, 2H), 1.69-1.57 (m, 2H), 1.48 (m, 1H); $^{13}$C NMR δ 157.8 (s), 135.6 (d), 134.0 (s), 132.8 (d), 131.0, 130.6, 123.1 (3 q), 117.3 (d), 114.3 (s), 88.7, 55.3 (2 d), 36.1, 30.9, 23.5 (3 t).

4-(3a,4,5,6,7,7a-Hexahydro-benzo[d]isoxazol-3-yl)-benzo-nitrile (87)

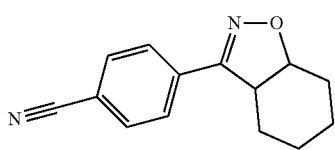 [SMILES: N#Cc1ccc(C2=NOC3CCCCC23)cc1]

Yield 67%, a colorless viscous oil; $^1$H NMR δ 7.81 (m, 2H), 7.69 (m, 2H), 4.56 (m, 1H), 3.26 (m, 1H), 2.30 (m, 1H), 1.97 (m, 1H), 1.79 (m, 1H), 1.75-1.64 (m, 2H), 1.55 (m, 1H), 1.32-1.21 (m, 2H). MS(EI) obs. 226.10.

4-(3a,4,5,6,7,7a-Hexahydro-benzo[d]isoxazol-3-yl)-2-trifluoromethyl benzonitrile (88)

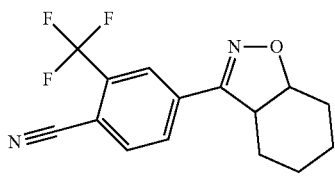 [SMILES: N#Cc1ccc(C2=NOC3CCCCC23)cc1C(F)(F)F]

Yield 93%, a yellow wax; $^1$H NMR δ 8.12 (d, 1H, J=0.8), 7.97 (dd, 1H, J=8.1, 0.8), 7.88 (d, 1H, J=8.1), 4.59 (m, 1H), 3.29 (m, 1H), 2.31 (m, 1H), 1.98 (m, 1H), 1.81 (m, 1H), 1.75-1.62 (m, 2H), 1.55 (m, 1H), 1.35-1.18 (m, 2H); $^{13}$C NMR δ 162.0 (s), 135.6, 134.8 (2 d), 133.8 (q), 130.2 (d), 125.1, 122.5 (2 q), 115.5 (d), 110.9 (s), 82.3, 43.9 (2 d), 26.6, 25.2, 22.3, 20.3 (4 t).

4-(3a,4,5,6,7,7a-Hexahydro-benzo[d]isoxazol-3-yl)-3-trifluoromethyl benzonitrile (89)

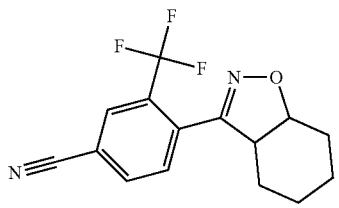 [SMILES: N#Cc1ccc(C2=NOC3CCCCC23)c(C(F)(F)F)c1]

Yield 67%, a yellow wax; ¹H NMR δ 8.05 (s, 1H), 7.89 (d, 1H, J=8.0), 7.69 (d, 1H, J=8.0), 4.67 (m, 1H), 3.37 (m, 1H), 2.13 (m, 1H), 1.83 (m, 1H), 1.69 (m, 1H), 1.59-1.45 (m, 3H), 1.32-1.24 (m, 2H); ¹³C NMR δ 162.1 (s), 135.6 (d), 134.0 (s), 132.6 (d), 130.9, 130.7, 123.1 (3 q), 117.4 (d), 114.5 (s), 81.3, 48.1 (2 d), 25.7, 25.5, 22.2, 20.4 (4 t).

4-(4,5,6,7,8,8a-Hexahydro-3aH-cyclohepta[d]isoxazol-3-yl)-2-trifluoromethyl-benzonitrile (90)

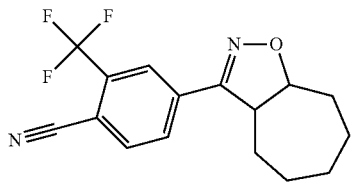 [SMILES: N#Cc1ccc(C2=NOC3CCCCCC23)cc1C(F)(F)F]

Yield 81%, a yellow wax; ¹H NMR δ 8.07 (d, 1H, J=0.8), 7.87 (dd, 1H, J=8.1, 0.8), 7.88 (d, 1H, J=8.1), 4.94 (m, 1H), 3.71 (m, 1H), 2.05 (m, 1H), 1.98 (m, 1H), 1.83-1.47 (m, 6H), 1.45-1.36 (m, 2H); ¹³C NMR δ 158.2 (s), 135.6, 134.9 (2 d), 133.8 (q), 130.4 (d), 125.3, 122.5 (2 q), 115.6 (d), 110.7 (s), 86.9, 50.8 (2 d), 31.3, 30.4, 28.4, 27.4, 24.0 (5 t).

4-(4,5,6,7,8,8a-Hexahydro-3aH-cyclohepta[d]isoxazol-3-yl)-3-trifluoromethyl benzonitrile (91)

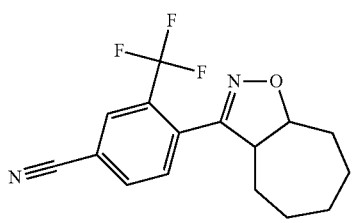 [SMILES: N#Cc1ccc(C2=NOC3CCCCCC23)c(C(F)(F)F)c1]

Yield 78%, a yellow wax; ¹H NMR δ 8.04 (s, 1H), 7.88 (d, 1H, J=8.0), 7.64 (d, 1H, J=8.0), 4.97 (m, 1H), 3.77 (m, 1H), 2.07 (m, 1H), 1.94 (m, 1H), 1.85 (m, 1H), 1.74-1.25 (m, 5H); ¹³C NMR δ 158.3 (s), 135.5 (d), 134.0 (s), 132.9 (d), 131.3, 130.9, 123.0 (3 q), 117.3 (d), 114.3 (s), 86.2, 54.6 (2 d), 31.5, 30.7, 28.5, 27.5, 24.5 (5 t).

4-(3a,4,5,6,7,8,9,9a-Octahydro-cycloocta[d]isoxazol-3-yl)-2-trifluoromethyl-benzonitrile (92)

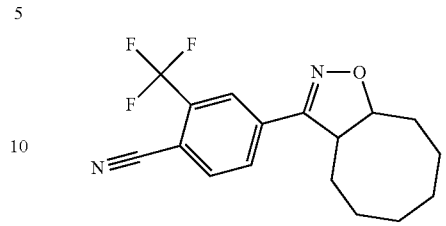

Yield 98%, a yellow wax; ¹H NMR δ 8.07 (s, 1H), 7.86-7.82 (m, 2H), 4.56 (m, 1H), 3.40 (m, 1H), 2.15-2.08 (m, 1H), 2.01 (m, 1H), 1.81-1.70 (m, 4H), 1.65 (m, 1H), 1.55-1.43 (m, 2H), 1.35-1.21 (m, 3H); ¹³C NMR δ 160.4 (s), 135.6, 134.8 (2 d), 133.8 (q), 130.3 (d), 125.3, 122.5 (2 q), 115.5 (d), 110.7 (s), 87.6, 49.6 (2 d), 30.3, 25.8, 25.6, 25.6, 25.2, 24.9 (6 t).

4-(3a,4,5,6,7,8,9,9a-Octahydro-cycloocta[d]isoxazol-3-yl)-3-trifluoromethyl-benzonitrile (93)

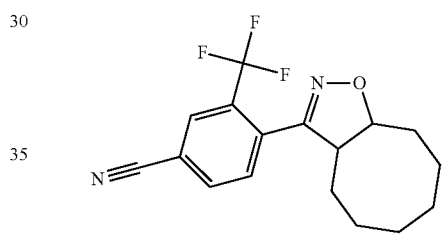

Yield 18%, a yellow wax; ¹H NMR δ 8.01 (s, 1H), 7.86 (d, 1H, J=8.0), 7.62 (d, 1H, J=8.0), 4.68 (m, 1H), 3.48 (m, 1H), 2.05-1.93 (m, 2H), 1.75-1.44 (m, 6H), 1.43-1.07 (m, 4H); ¹³C NMR δ 159.9 (s), 135.5 (d), 134.2 (s), 133.2 (d), 130.9, 130.7, 123.0 (3 q), 117.3 (d), 114.4 (s), 86.7, 53.8 (2 d), 30.0, 26.6, 26.3, 25.7, 25.6, 24.4 (6 t).

3-(3a,4,5,6,7,7a-Hexahydro-benzo[d]isoxazol-3-yl)-2-trifluoromethyl-benzonitrile (94)

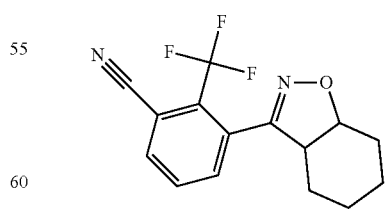

Yield 17%, yellow viscous oil ¹H NMR δ 7.92 (d, 1H, J=7.5), 7.73 (dd, 1H, J=8.3, 7.5), 7.71 (d, 1H, J=8.3), 4.66 (m, 1H), 3.25 (m, 1H), 2.16 (m, 1H), 2.01 (m, 1H), 1.71 (m, 1H), 1.66 (m, 1H), 1.58 (m, 1H), 1.51 (m, 1H), 1.25-1.18 (m, 2H).

3-(4,5,6,7,8,8a-Hexahydro-3aH-cyclohepta[d]isoxazol-3-yl)-2-trifluoromethyl-benzonitrile (95)

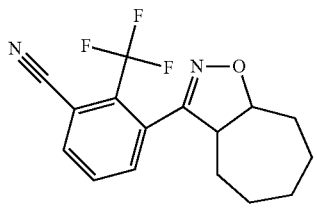 [SMILES: N#Cc1cccc(C2=NOC3CCCCCC23)c1C(F)(F)F]

Yield 34%, yellow viscous oil $^1$H NMR δ 7.91 (d, 1H, J=7.5), 7.72 (dd, 1H, J=8.3, 7.5), 7.66 (d, 1H, J=8.3), 4.95 (m, 1H), 3.66 (m, 1H), 2.10 (m, 1H), 1.94 (m, 1H), 1.87 (m, 1H), 1.75-1.43 (m, 6H), 1.13 (m, 1H).

Chiral Separations of the Racemic Mixtures.

The enantiomers were separated by semi preparative HPLC using a Regis Technologies (R,R)-Whelk-O 1 (25 cm×10 mm i.d.) chiral stationary phase in Hexane/i-PrOH/AcOH 90/10/0.5 at flow rate 5 mL/min.

Competitive AR Binding Assay.

AR binding was measured by a competitive assay against [$^3$H]-R1881 (PerkinElmer) in transiently transfected COS-1 cells. One day before transfection, COS-1 cells were seeded into 2 ml of DMEM (Dulbecco's modified Eagle medium, Gipco) with 10% dextran-charcoal-treated fetal bovine serum and 0.25% (vol/vol) Penicillin-Streptomysin (Euroclone) at a density of 140×10$^3$ cells/well. After medium change to DMEM 2.5% FBS, the cells were transfected for 24 hours with 10 ng/well of human AR expression vector pSG5 hAR by using the TransIT method (Micrus Bio TransIT LT1, Transfection Reagent). After 36 hours, the cells where treated with tested compounds using 10000 fold molarities compared to labelled R1881 (1.34 nM). After 2 hours of incubation at 37° C., the medium was removed. The cells were removed from the wells to 150 μl of 1× phosphate buffered saline (PBS), transferred to Eppendorf tubes and centrifuged at 4° C. using 4000×g for 5 min, and then washed twice with 150 μl of PBS. The cell pellets were dissolved to 50 μl of 0.5M NaOH and incubated for 15 min at 56° C., after which the samples (three replicates for each sample compound) were transferred to liquid twinkle tubes with 3 ml of OptiPhase HiSafe 3 twinkle solution (PerkinElmer) and radioactivity of AR-bound [$^3$H]-R1881 determined. The results were measured with LKB WALLAC 1214 racbeta equipment. The ability of test compounds to bind AR is reported as reduction in bound radioactivity obtained with 1.34 nM [$^3$H]-R1881.

The results (% inhibition) were calculated as:

% inhibition=100−[100×(average$_{compound}$/average$_{[3H]-R1881}$)].

The results are shown in Tables 1-3.

TABLE 1

AR binding assay. Inhibition (%) of [$^3$H]-R1881 binding. Complete inhibition equals to 100%.

| Compound of Example No. (13.4 μM) | Inhibition of [$^3$H]-R1881 binding at 1.34 nM ± S.D. | Compound of Example No. | Inhibition of [$^3$H]-R1881 binding at 1.34 nM ± S.D. |
|---|---|---|---|
| Hydroxyflutamide[a] | 91.1 ± 2.2 | 32a | 30.5 ± 5.4 |
| 2ab[b] | 64.2 ± 2.2 | 32b | 0 |
| 3ab | 49.6 ± 2.0 | 33a | 68.4 ± 1.9 |
| 4ab | 69.9 ± 3.3 | 33b | 56.9 ± 4.4 |
| 5a[c] | 42.7 ± 6.6 | 34a | 34.7 ± 2.7 |
| 5b[d] | 59.7 ± 2.7 | 34b | 0 |
| 6ab | 31.4 ± 1.9 | 37ab | 93.5 ± 0.9 |
| 7ab | 51.0 ± 2.4 | 38a | 94.5 ± 0.5 |
| 8ab | 30.4 ± 2.9 | 38b | 90.7 ± 0.5 |
| 9ab | 63.7 ± 1.5 | 50a | 63.8 ± 1.8 |
| 12a | 55.9 ± 1.1 | 50b | 55.7 ± 1.9 |
| 12b | 30.2 ± 6.0 | 53ab | 29.8 ± 10.8 |
| 13a | 31.1 ± 5.6 | 54ab | 28.2 ± 3.0 |
| 13b | 1.6 ± 6.6 | 55a | 35.1 ± 5.8 |
| 14a | 29.6 ± 3.4 | 55b | 32.7 ± 3.5 |
| 14b | 0 | 57ab | 48.7 ± 3.3 |
| 15ab | 49.5 ± 4.3 | 58ab | 8.2 ± 1.3 |
| 27a | 17.0 ± 7.0 | 59ab | 39.1 ± 2.6 |
| 27b | 0 | 61a | 14.9 ± 1.8 |
| 30a | 30.2 ± 3.8 | 61b | 0 |
| 30b | 66.3 ± 6.5 | 65a | 0 |
| 31a | 20.3 ± 9.9 | 65b | 13.5 ± 1.6 |
| 31b | 0 | 66ab | 17.8 ± 2.4 |
| | | 68ab | 14.7 ± 1.0 |

[a]Hydroxyflutamide (active form of flutamide, which is an oral antiandrogen drug primarily used to treat prostate cancer) was used as a reference compound.
[b]ab = enantiomers not separated, rasemic mixture tested.
[c]a = enantiomer with a shorter retention time in the chiral separation.
[d]b = enantiomer with a longer retention time in the chiral separation.

TABLE 2

AR binding assay. Inhibition (%) of [$^3$H]-R1881 binding. Complete inhibition equals to 100%.

| Compound of Example No. (13.4 μM) | Inhibition of [$^3$H]-R1881 binding at 1.34 nM ± S.D. | Compound of Example No. | Inhibition of [$^3$H]-R1881 binding at 1.34 nM ± S.D. |
|---|---|---|---|
| Hydroxyflutamide[a] | 94.8 ± 0.8 | 43a | 66.3 ± 9.8 |
| 19ab[b] | 84.6 ± 4.9 | 43b | 76.0 ± 0.3 |
| 35ab | 88.5 ± 4.2 | 85a | 87.6 ± 0.3 |
| 36a[c] | 84.6 ± 0.7 | 85b | 91.8 ± 1.7 |
| 36b[d] | 87.7 ± 3.0 | 88ab | 99.2 ± 0.5 |
| 39ab | 55.7 ± 5.8 | 89a | 78.8 ± 0.6 |
| 40a | 88.8 ± 3.1 | 89b | 83.6 ± 0.9 |
| 40b | 92.2 ± 0.7 | 90ab | 98.7 ± 0.6 |
| 41ab | 97.8 ± 0.5 | 91a | 85.4 ± 1.5 |
| 42a | 90.5 ± 3.1 | 91b | 87.4 ± 2.7 |
| 42b | 89.5 ± 2.0 | 92ab | 85.8 ± 1.3 |

[a-d]See Table 1.

TABLE 3

AR binding assay. Inhibition (%) of [$^3$H]-R1881 binding. Complete inhibition equals to 100%.

| Compound of Example No. (13.4 μM) | Inhibition of [$^3$H]-R1881 binding at 1.34 nM ± S.D. | Compound of Example No. | Inhibition of [$^3$H]-R1881 binding at 1.34 nM ± S.D. |
|---|---|---|---|
| Hydroxyflutamide[a] | 95.2 ± 2.9 | 45ab | 85.7 ± 3.8 |
| 20a | 89.3 ± 3.8 | 46a | 86.4 ± 1.8 |
| 20b | 85.3 ± 2.8 | 46b | 90.4 ± 3.8 |
| 21a | 69.7 ± 4.5 | 86ab | 91.7 ± 1.7 |
| 21b | 90.9 ± 0.9 | 93a | 87.2 ± 2.9 |
| 22ab[b] | 89.3 ± 4.7 | 93b | 76.0 ± 4.8 |

TABLE 3-continued

AR binding assay. Inhibition (%) of [$^3$H]-R1881 binding.
Complete inhibition equals to 100%.

| Compound of Example No. (13.4 μM) | Inhibition of [$^3$H]-R1881 binding at 1.34 nM ± S.D. | Compound of Example No. | Inhibition of [$^3$H]-R1881 binding at 1.34 nM ± S.D. |
|---|---|---|---|
| 42a[c] | 91.4 ± 3.8 | 94a | 97.4 ± 0.4 |
| 42b[d] | 89.3 ± 4.8 | 94b | 97.6 ± 0.2 |
| 44a | 90.3 ± 2.7 | 95a | 96.2 ± 0.8 |
| 44b | 85.2 ± 3.8 | 95b | 98.1 ± 0.3 |

[a-d]See Table 1.

Determination of the Antiandrogen Activity.

Testosterone was bought from Sigma Chemical Co. (St. Louis, Mo.) and hydroxyflutamide from Chemos GmbH. One day before transfection, COS-1 cells (from ATCC) were seeded into 1 ml of DMEM (Dulbecco's modified Eagle medium, Gibco) with 10% dextran-charcoal-treated fetal bovine serum and 0.25% (vol/vol) Penicillin-Streptomycin (Euroclone) at a density of 70×10$^3$ cells/well. After medium change to DMEM 2.5% FBS, the cells were transfected for 24 hours with 10 ng/well of human AR expression vector pSG5-hAR, 100 ng/well of reporter plasmid Probasin-luc, and 10 ng/well of control plasmid pCMV-β-gal by using the TransIT method (Micrus Bio TransIT LT1, Transfection Reagent). After the transfection, the cells received treatment of test compounds giving final concentration of 10 μM for each compound. In the antagonist test the wells were also treated with 100 nM final concentration of testosterone. After 18 hours, the cells were washed, lysed and assayed for luciferase and normalization for β-galactosidase activities and protein concentrations. The cells were washed with 100 μl of cold phosphate buffered saline (PBS) and lysed with 35 μl 1× Reporter lysis Buffer (Promega) and frozen (−70° C.) for 30 minutes. Cell lysates were placed in 1.5-ml propylene tubes and centrifuged at 13200×g for 5 minutes at room temperature. For β-galactosidase assay 10 μl of supernatant from each cell extract was transferred to a 96-well plate (96 well Elisa Microplates, PS, Microcon) and incubated for 10 minutes at 37° C. with 65 μl of reaction mixture consisting 0.76 μl 100×Mg-buffer, 12.5 μl ONPG (4 mg/ml), and 54.3 μl of sodium-phosphate buffer (pH 7). The reaction was stopped with treatment of 125 μl Na$_2$CO$_3$. For luciferase assay 10 μl of the supernatant was transferred to a 96-well plate (Greiner Microlon lumitrac 200) and treated with 30 μl of luciferase assay substrate solution (Promega Luciferase Assay System E1501). For the study of protein concentrations 5 μl of the supernatant was transferred to a 96-well plate (Elisa Microplates, PS, Microcon) and mixed with 200 μl of Bio-rad protein assay reagent. The luciferase activities were measured with Thermo Luminoscan Ascent scanner and the protein concentrations and β-galactosidase activities with Thermo Labsystem Multiscan Ex scanner. Also blank and control samples were measured. During the maintenance, transfection, and treatment with tested compounds the cells were incubated in humidified atmosphere with 5% carbon dioxide at 37° C. The results are shown in Table 4 and FIG. 1.

TABLE 4

AR antagonism assay. Inhibition of transcriptional activation of AR by the novel non-steroidal compounds. Values are percentages of the relative luciferase response, which equals to 100% for testosterone (no antiandrogenic effect) and 0% for complete antagonism.

| Compound of Example No. (10.0 μM) | AR antagonism against 100 nM testosterone ± S.D. | Compound of Example No. | AR antagonism against 100 nM testosterone ± S.D. |
|---|---|---|---|
| Hydroxy-flutamide | 13.0 ± 1.1 | 42a | 17.4 ± 1.5 |
| 19ab[b] | 54.6 ± 2.3 | 42b | 25.5 ± 1.5 |
| 20a[c] | 23.2 ± 0.5 | 43a | 57.7 ± 9.9 |
| 20b[d] | 37.4 ± 7.3 | 43b | 56.6 ± 1.4 |
| 21a | 19.2 ± 6.8 | 44a | 19.8 ± 0.5 |
| 21b | 22.9 ± 4.9 | 44b | 35.6 ± 7.8 |
| 22ab | 21.8 ± 4.1 | 45ab | 27.8 ± 1.0 |
| 23ab | 40.9 ± 2.4 | 46a | 3.1 ± 1.7 |
| 26a | 25.7 ± 5.5 | 46b | 2.2 ± 0.8 |
| 26b | 41.0 ± 1.6 | 85a | 44.9 ± 3.6 |
| 32a | 40.9 ± 2.4 | 85b | 18.9 ± 0.5 |
| 32b | 91.4 ± 7.7 | 86ab | 29.3 ± 3.7 |
| 33a | 40.2 ± 7.1 | 88ab | 9.2 ± 1.7 |
| 33b | 100 | 89a | 27.5 ± 4.1 |
| 34ab | 48.0 ± 6.7 | 89b | 20.3 ± 1.7 |
| 35ab | 53.4 ± 5.4 | 90ab | 12.6 ± 0.7 |
| 36a | 49.7 ± 5.1 | 91a | 29.8 ± 3.6 |
| 36b | 30.0 ± 6.1 | 91b | 27.2 ± 4.8 |
| 37ab | 10.6 ± 1.6 | 92ab | 24.0 ± 1.7 |
| 38a | 2.9 ± 0.5 | 93a | 9.4 ± 0.3 |
| 38b | 75.9 ± 3.7 | 93b | 65.5 ± 9.0 |
| 39ab | 43.8 ± 2.4 | 94a | 17.8 ± 3.9 |
| 40a | 28.8 ± 2.0 | 94b | 5.4 ± 1.7 |
| 40b | 15.6 ± 0.8 | 95a | 14.4 ± 1.9 |
| 41ab | 10.1 ± 0.9 | 95b | 19.2 ± 2.9 |

[a-d], see Table 1.

Determination of AR-Dependent Gene Expression in Prostate Cancer Cells by Quantitative Real-Time RT-PCR.

Figure 2A:
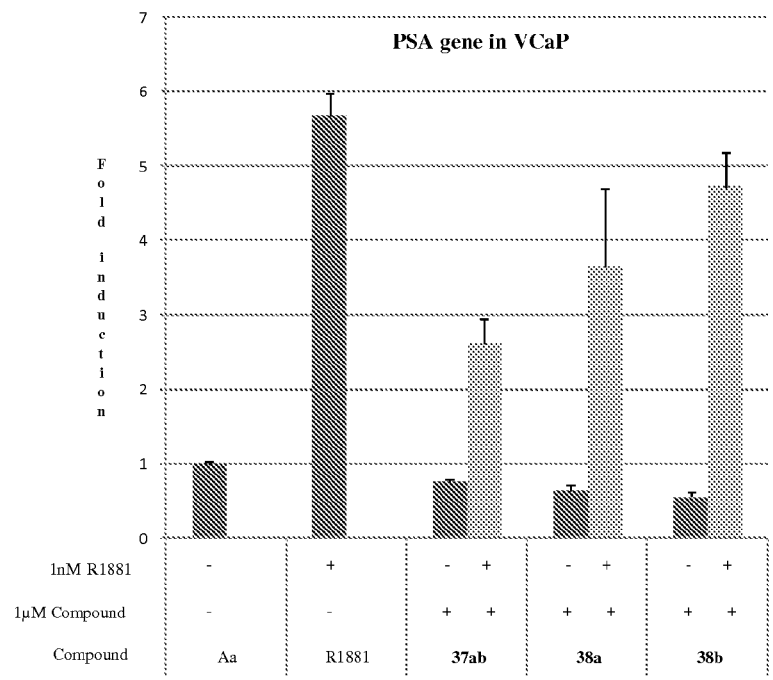
FIGS. 2A, 2B illustrates the relative levels of prostate specific antigen (PSA) mRNA in VCaP (expressing wild-type AR) and LNCaP (containing an AR mutation, which turns hydroxyflutamide to an agonist) prostate cancer cells in the presence of vehicle (Aa, ethanol), R1881 (synthetic AR agonist), novel non-steroidal compound alone or together with R1881 as indicated.
Figure 2B:
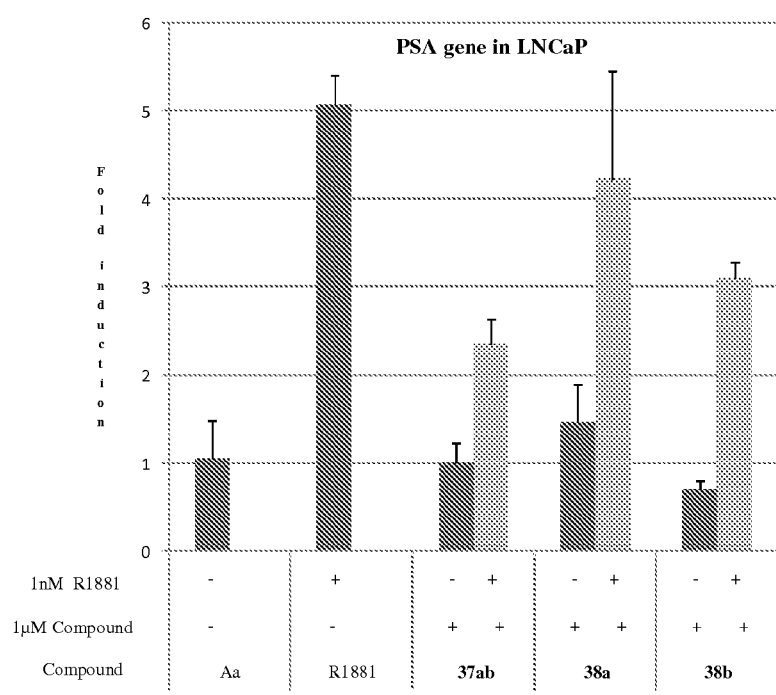
Figure 3A:
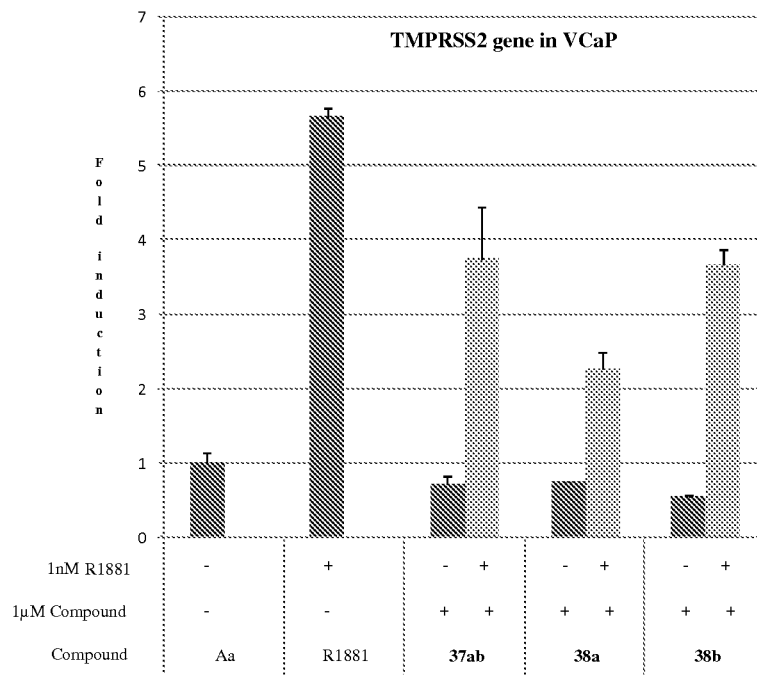
FIGS. 3A, 3B shows the relative levels of TMPRSS2 mRNA in VCaP and LNCaP prostate cancer cells in the presence of different compounds. See FIGS. 2A and 2B for the interpretation of the graph.
Figure 3B:
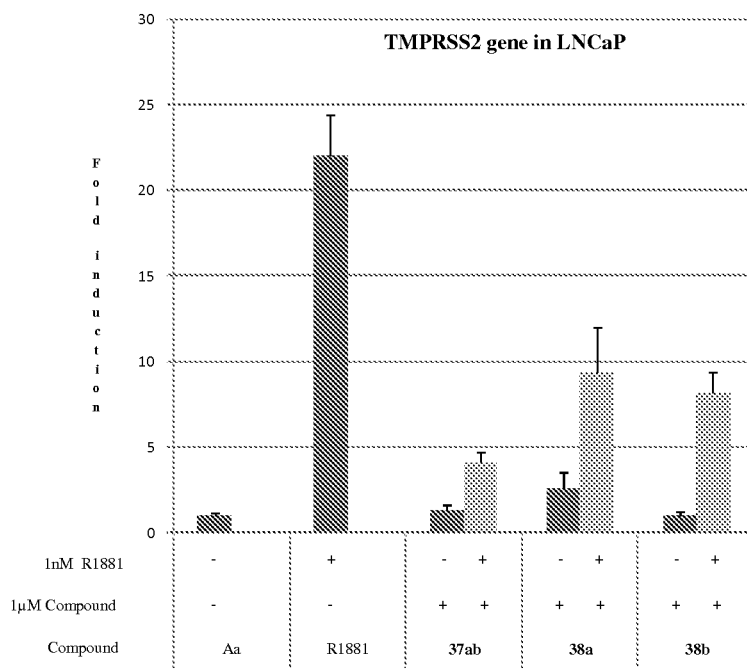
Figure 4A:
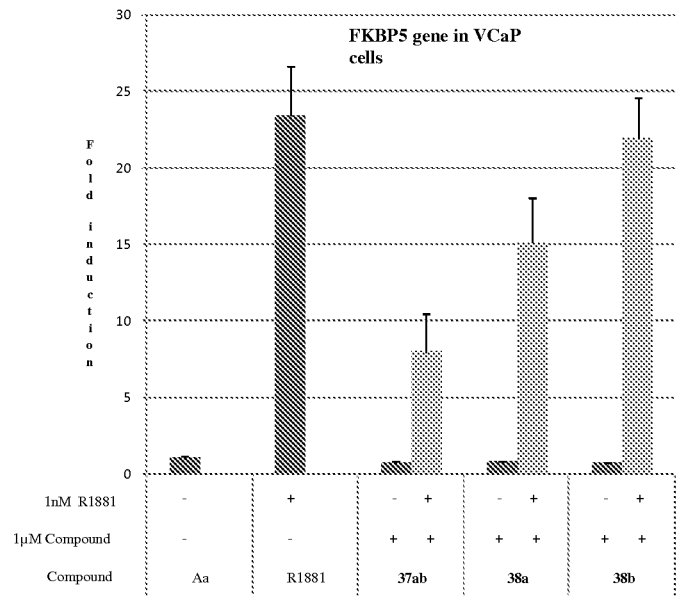
FIGS. 4A, 4B shows the relative levels of FKBP5 mRNA in VCaP and LNCaP prostate cancer cells in the presence of different compounds. See FIGS. 2A and 2B for the interpretation of the graph.
Figure 4B:
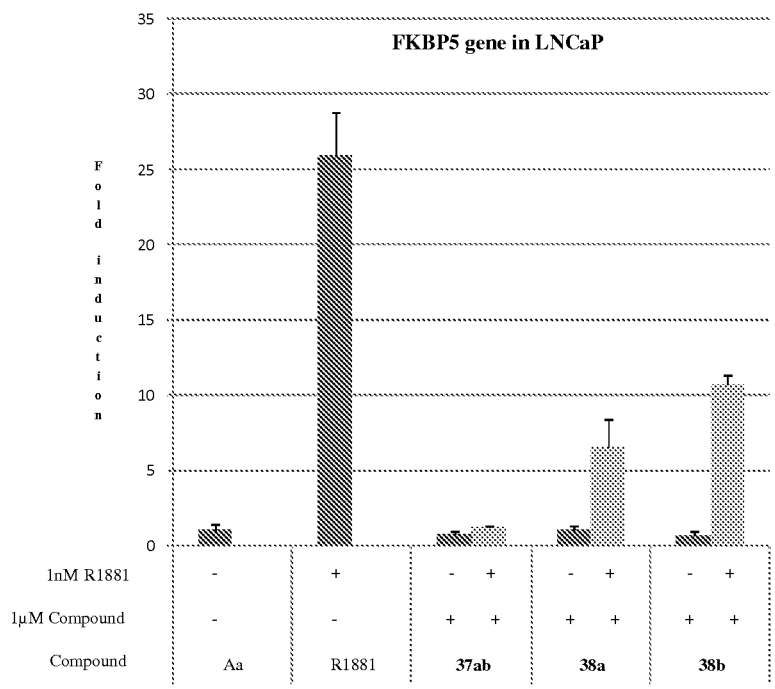

LNCaP or VCaP prostate cancer cells (from ATCC) were splitted on day 1 on 12-well plates (140 000 cells/well). After 24 hours the cells were treated with the test compounds. Total RNA was prepared after 17-18 hours of the treatment using Trizol reagent (Invitrogen) according to the manufacturer's instructions; amounts of solutions used for 12-well format were 500 μl Trizol, 100 μl chloroform, 250 μl isopropanol, 500 μl 75% (v/v) ethanol and the RNA pellets were suspensed on 15 μl sterile H$_2$O. RNA concentrations were determined with Nanodrop using 1 μl of RNA. All samples were diluted into equal concentration with sterile H$_2$O. The cDNA syntheses were done using 1 μg of RNA with Roche Transcriptor First Strand cDNA Synthesis Kit according to the manufacturer's instructions. The cDNA was diluted to 1:5 by adding 80 μl sterile H$_2$O into each sample. Five μl of diluted cDNA, 1 μl primer mix (containing 4 μM of each primer for PSA, TMPRSS2, FKBP51, or GAPDH), 12.5 μl of 2×SYBR-master mix (Roche), and 6.5 μl of H$_2$O were used for real-time PCR with Mx3000P Real-Time PCR System (Stratagene). Analyzed GAPDH mRNA levels were used to normalize the amounts of total RNA between the samples. Fold changes were calculated using the formula $2^{-(\Delta\Delta Ct)}$, where $\Delta\Delta Ct$ is $\Delta Ct_{(R1881)} - \Delta Ct_{(EtOH)}$, $\Delta Ct$ is $Ct_{(gene\ X)} - Ct_{(GAPDH)}$ and Ct is the cycle at which the threshold is crossed. The results are shown in FIGS. 2-4.

The invention claimed is:
1. A compound selected from the group consisting of 5-benzyl-3-(4-nitrophenyl)-5-phenyl-4,5-dihydro-isoxazole (17), 4-(5-benzyl-5-phenyl-4,5-dihydro-isoxazol-3-yl)-benzonitrile (18), 3-(4-fluoro-2-trifluoromethyl-phenyl)-4,5,6,6a-tetrahydro-3aH-cyclopenta[d]-isoxazole (20), 3-(4-nitro-3-trifluoromethyl-phenyl)-4,5,6,6a-tetrahydro-3aH- cyclopenta[d]-isoxazole (21), 3-(4-fluoro-3-trifluoromethyl-phenyl)-3a,4,5,6,7,7a-hexahydro-benzo-[d]-isoxazole (35), 3-(4-fluoro-2-trifluoromethyl-phenyl)-3a,4,5,6,7,7a-hexahydro-benzo[d]-isoxazole (36), 3-(4-nitro-3-trifluoromethyl-phenyl)-3a,4,5,6,7,7a-hexahydro-benzo[d]isoxazole (37), 3-(4-nitro-2-trifluoro-methyl-phenyl)-3a,4,5,6,7,7a-hexahydro-benzo[d]-isoxazole (38), 3-(4-fluoro-2-tri-fluoromethyl-phenyl)-4,5,6,7,8,8a-hexahydro-3aH-cyclohepta [d]isoxazole (40), 3-(4-nitro-3-trifluoromethyl-phenyl)-4,5, 6,7,8,8a-hexahydro-3aH-cyclohepta[d]-isoxazole (41), 3-(4-nitro-2-trifluoromethyl-phenyl)-4,5,6,7,8,8a-hexahydro-3aH-cyclohepta[d]isoxazole (42), 3-(4-fluoro-2-trifluoromethyl-phenyl)-3a,4,5,6,7,8,9,9a-octahydro-cycloocta[d]isoxazole (44), 3-(4-nitro-2-trifluoro-methyl-phenyl)-3a,4,5,6,7,8,9,9a-octahydro-cycloocta[d]isoxazole (46), 5-benzyl-4-butyl-3-(3-chloro-phenyl)-5-methyl-4,5-dihydro-[1,2,4]oxadiazole (50), 5-benzyl-4-butyl-5-methyl-3-(4-nitro-phenyl)-4,5-dihydro-[1,2,4]oxadiazole (51), 4-(5-benzyl-4-butyl-5-methyl-4,5-dihydro-[1,2,4]oxadiazol-3-yl)-benzonitrile (52), 4-(5-benzyl-4-isobutyl-5-methyl-4,5-dihydro-[1,2,4]oxadiazol-3-yl)-benzonitrile (62), 4-(4,5,6, 6a-tetrahydro-3aH-cyclo-penta[d]isoxazol-3-yl)-2-trifluoromethyl-benzonitrile (85), 4-(4,5,6,6a-tetrahydro-3aH-cyclopenta[d]isoxazol-3-yl)-3-trifluoromethyl-benzonitrile (86), 4-(3a,4,5,6,7,7a-hexahydro-benzo[d] isoxazol-3-yl)-2-trifluoromethyl-benzonitrile (88), 4-(3a,4, 5,6,7,7a-hexahydro-benzo[d]isoxazol-3-yl)-3-trifluoromethyl-benzo-nitrile (89), 4-(4,5,6,7,8,8a-hexahydro-3aH-cyclohepta[d]isoxazol-3-yl)-2-trifluoromethyl-benzonitrile (90), 4-(4,5,6,7,8,8a-hexahydro-3aH-cyclohepta[d]isoxazol-3-yl)-3-trifluoromethyl-benzonitrile (91), 4-(3a,4,5,6,7,8,9,9a-octahydro-cycloocta-[d]isoxazol-3-yl)-2 trifluoromethyl-benzonitrile (92), and 4-(3a,4,5,6,7,8,9,9a-octa-hydro-cycloocta[d]isoxazol-3-yl)-3-trifluoromethyl-benzonitrile (93).

2. A compound selected from the group consisting of methyl 3-(3-chloro-phenyl)-4,5,6,6a-tetrahydro-3aH-cyclopenta[d]isoxazole-5-carboxylate (69), 3-(3-Chloro-phenyl)-4,5,6,6a-tetrahydro-3aH-cyclopenta[d]isoxazole-5-carboxylic acid (70), 3-(4-Fluoro-3-trifluoromethyl-phenyl)-4,5,6, 6a-tetrahydro-3aH-cyclopenta[d]isoxazol-5-ylmethyl acetate (71), [3-(4-Fluoro-3-trifluoromethyl-phenyl)-4,5,6, 6a-tetrahydro-3aH-cyclopenta[d]isoxazol-5-yl]-methanol (72), 2-[3-(4-Fluoro-3-trifluoromethyl-phenyl)-4,5,6,6a-tetrahydro-3aH-cyclopenta[d]isoxazol-6-yl]-ethyl acetate (73), 2-[3-(4-Fluoro-3-trifluoromethyl-phenyl)-4,5,6,6a-tetrahydro-3aH-cyclopenta[d]isoxazol-4-yl]-ethyl acetate (74), 3-(4-Chloro-phenyl)-4,5,6,7,8,8a-hexahydro-3aH-cyclohepta[d]isoxazol-8-yl acetate (75), 3-(4-Chloro-phenyl)-4,5, 6,7,8,8a-hexahydro-3aH-cyclohepta[d]isoxazol-4-yl acetate (76), 3-(4-Chloro-phenyl)-4,5,6,7,8,8a-hexahydro-3aH-cyclohepta[d]isoxazol-8-ol (77), 3-(3a,4,5,6,7,7a-Hexahydro-benzo[d]isoxazol-3-yl)-2-trifluoromethyl-benzonitrile (94) and 3-(4,5,6,7,8,8a-Hexahydro-3aH-cyclohepta[d]isoxazol-3-yl)-2-trifluoromethyl-benzonitrile (95).

* * * * *